(12) United States Patent
Deban et al.

(10) Patent No.: US 12,171,791 B2
(45) Date of Patent: Dec. 24, 2024

(54) CANCER THERAPY WITH LIVE ATTENUATED BACTERIA

(71) Applicant: Prokarium Limited, London (GB)

(72) Inventors: Livija Deban, London (GB); Nicholas Glanville, London (GB)

(73) Assignee: Prokarium Limited, London (GB)

( * ) Notice: Subject to any disclaimer, the term of this patent is extended or adjusted under 35 U.S.C. 154(b) by 0 days.

(21) Appl. No.: 18/559,543

(22) PCT Filed: Jul. 28, 2022

(86) PCT No.: PCT/EP2022/071198
§ 371 (c)(1),
(2) Date: Nov. 7, 2023

(87) PCT Pub. No.: WO2023/006879
PCT Pub. Date: Feb. 2, 2023

(65) Prior Publication Data
US 2024/0226190 A1    Jul. 11, 2024

(30) Foreign Application Priority Data
Jul. 28, 2021 (EP) .................................. 21188352

(51) Int. Cl.
| | | |
|---|---|---|
| *A61K 35/74* | (2015.01) | |
| *A61K 39/00* | (2006.01) | |
| *A61K 39/112* | (2006.01) | |
| *A61P 35/00* | (2006.01) | |

(52) U.S. Cl.
CPC .......... *A61K 35/74* (2013.01); *A61K 39/0275* (2013.01); *A61P 35/00* (2018.01); *A61K 2039/522* (2013.01); *A61K 2039/585* (2013.01)

(58) Field of Classification Search
CPC .................................................... A61K 35/74
See application file for complete search history.

(56) References Cited

U.S. PATENT DOCUMENTS

2007/0298012 A1    12/2007  King et al.
2016/0074441 A1     3/2016  Nardelli Haefliger et al.

FOREIGN PATENT DOCUMENTS

| WO | 00/68261 A | 11/2000 |
| WO | 03/063593 A1 | 8/2003 |
| WO | 2006076678 A2 | 7/2006 |
| WO | 2009098246 A1 | 8/2009 |
| WO | 2010079343 A2 | 7/2010 |
| WO | WO 2014/180929 A1 * | 11/2013 |
| WO | WO 2019/110819 A1 * | 6/2019 |

OTHER PUBLICATIONS

Stratford et al., Infections and Immunity, 2005, 73(1): 362-368 (Year: 2005).*
Chorobik et al., "*Salmonella* and cancer: from pathogens to therapeutics," Acta Biochmica Polonica, 60(3):285-297, 2013.
Zhou et al., "Tumour-targeting bacteria engineered to fight cancer," Nature Reviews Cancer, 18(12):727-743, 2018.
Pilling, Stephen, International Search Report & Written Opinion, European Patent Office, PCT/EP2022/071198, Oct. 28, 2022.

* cited by examiner

*Primary Examiner* — Brian Gangle
*Assistant Examiner* — Lakia J Jackson-Tongue
(74) *Attorney, Agent, or Firm* — Gavrilovich, Dodd & Lindsey LLP

(57) ABSTRACT

The present invention relates to the field of cancer therapy. In particular, the present invention relates to a first composition comprising a live attenuated bacterium for use in the treatment, prevention, reduction, inhibition, prevention of recurrence, or control of a neoplastic disease in a subject being or intended to be administered a second composition comprising a live attenuated bacterium, said bacterium being the same or different to that of the first composition and methods thereof.

16 Claims, 12 Drawing Sheets

CANCER THERAPY WITH LIVE ATTENUATED BACTERIA

CROSS REFERENCE TO RELATED APPLICATIONS

This application is a U.S. National Phase Application filed under 35 U.S.C. § 371 and claim priority to International Application No. PCT/EP2022/071198, filed on Jul. 28, 2022, which application claims priority to European Application No: 21188352,5, filed Jul. 28, 2021, the disclosures of which are incorporated herein by reference in their entirety.

FIELD OF THE INVENTION

The present invention relates to the field of cancer therapy. In particular, the present invention relates to a method of preventing, treating or inhibiting the development of neoplastic disease in a subject.

BACKGROUND OF THE INVENTION

The field of cancer therapy is continually evolving with new therapies as our understanding of underlying mechanisms associated with cancer formation and progression improves. Presently, a patient diagnosed with cancer has numerous treatment options, including surgery, radiotherapy, chemotherapy and immunotherapy. However, despite the varied treatment options available to cancer patients, a significant portion of patients relapse, remain refractory to treatment or experience toxic side-effects that result in the discontinuation of the treatment. Accordingly, novel, efficacious and safe cancer treatment strategies continue to be required.

One therapeutic approach that has been adopted in the oncology field is that of using compositions comprising live attenuated bacteria. For example, one treatment strategy that has been at least partially successful in the field of bladder cancer is that of intravesical immunotherapy with *Bacillus* Calmette-Guerin (BCG). However, whilst BCG therapy has had some clinical success, it is estimated that close to 90% of patients experience some kind of adverse side effect, ranging from cystitis to sepsis and death, and that patient compliance in some instances is low due to the demanding dosing schedule (six consecutive weekly intravesical installations). Additionally, despite BCG being used in combination with other therapies in an effort to enhance efficacy, these combination therapies fail to ameliorate the side-effects disclosed above.

Isolated attempts to develop compositions comprising attenuated recombinant bacteria and/or attenuated tumour-targeted bacteria, including attenuated *Salmonella* Typhimurium, for the inhibition of the growth or reduction of the volume of a solid tumour cancer have been attempted, such as, e.g. WO03/063593 (Vion Pharmaceuticals); US2007/0298012 (I. King & L. M. Zheng); WO2009/098246 (Aeterna Zentaris GmbH); WO2006/076678 (Univ. John Hopkins). *Salmonella typhi* strains have also been proposed for use in the oncology field, for example, for the treatment of bladder cancer (see WO2014/180929). Zhou et al., (Nature Reviews Cancer, 18:12: 727-743, 2018) disclose tumour-targeting bacteria engineered to fight cancer and Chorobik et al., (Acta Biochimica Polonica, 60:3:285-297, 2013) discloses *Salmonella* as being a possible therapeutic in the context of cancer. However, numerous challenges remain with this approach, including sub-optimal levels of anti-cancer activity.

Accordingly, there remains a significant need in the cancer field for novel therapeutic strategies. Specifically, there remains a need for methods that have improved efficacy of said treatment in those individuals who respond positively. At the same time, there is a significant need for methods that show sustained efficacy in individuals who otherwise would be refractory to said treatment. Finally, there is a need for a therapeutic strategy in which patient compliance is improved.

SUMMARY OF THE INVENTION

The present invention provides an effective method for treating, preventing and/or preventing the recurrence of neoplastic disease in a subject by administering a first and second composition both comprising a live attenuated bacterium. The inventors have surprisingly found that this combination results in a more efficacious therapy than if the subject was treated with a single composition comprising the live attenuated bacteria i.e., a synergistic or additive effect is achieved. It is believed that the systemic modifications observed from administering the live attenuated bacteria of the first composition, in combination with the systemic immune memory generated against said live attenuated bacteria, can enhance the anti-tumour activity of the live attenuated bacteria of the second composition via enhancing the innate immune response and bystander effects of recruitment of effector memory cells, when the second composition is administered locally to the site of the neoplastic disease.

Accordingly, in a first aspect, the present invention provides for a first composition comprising a live attenuated bacterium for use in the treatment, prevention, reduction, inhibition, prevention of recurrence, or control of a neoplastic disease in a subject being or intended to be administered a second composition comprising a live attenuated bacterium, said bacterium being the same or different to that of the first composition, wherein the first composition is formulated for oral, intravenous, intranasal, intradermal or subcutaneous delivery to stimulate a systemic immune response in the subject and is for administration simultaneously, separately or sequentially with the second composition, and wherein the second composition is for administration locally to the site of the neoplastic disease.

In a second aspect, the present invention provides for a method of treating, preventing, reducing, inhibiting, preventing recurrence, or controlling a neoplastic disease in a subject, wherein the method comprises simultaneously, separately or sequentially administering to the subject, (i) a first composition comprising a live attenuated bacterium and (ii) a second composition comprising a live attenuated bacterium, said bacterium being the same or different to that of the first composition, wherein the first composition is formulated for oral, intravenous, intranasal, intradermal or subcutaneous delivery to stimulate a systemic immune response in the subject and is for administration simultaneously, separately or sequentially with the second composition, and wherein the second composition is for administration locally to the site of the neoplastic disease.

DESCRIPTION OF FIGURES

FIG. 1B shows the percentage survival of mice treated with subcutaneous systemic and local administration of

*Salmonella Typhi*. C57BL/6 mice were treated with ZH9 or had no treatment subcutaneously, inoculated with MB49 tumour cells to the bladder and treated with ZH9 or PBS control intravesically (ives). Survival was monitored over 100 days. The graph is a combination of results from 5 independent studies. Statistics are log-rank (Mantel-Cox) test. p<0.01. **p<0.0001.

Figure 2:
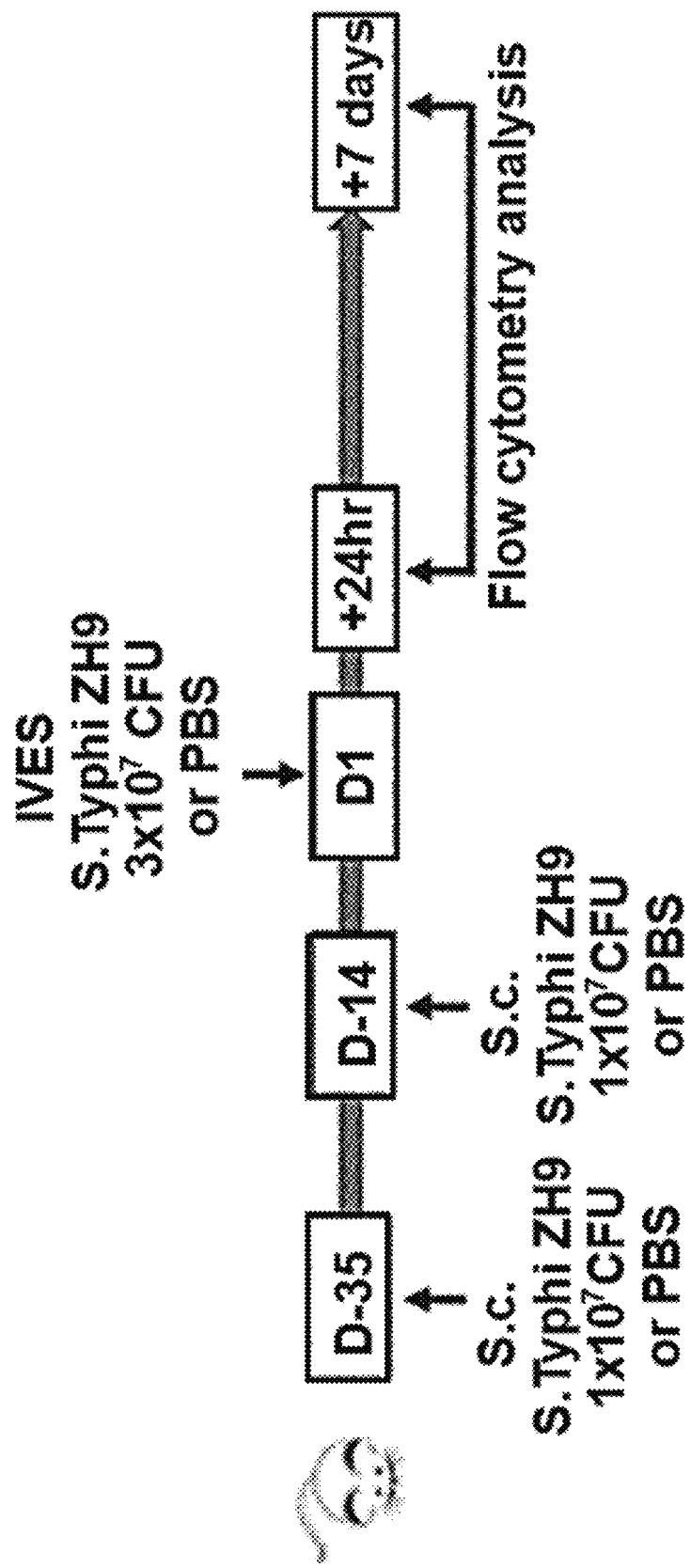

FIG. 2 shows a schematic demonstrating the timeline of flow cytometry analysis following subcutaneous systemic and local administration of *Salmonella typhi* in healthy mice. S.c, subcutaneous. IVES, intravesical.

Figure 3A:
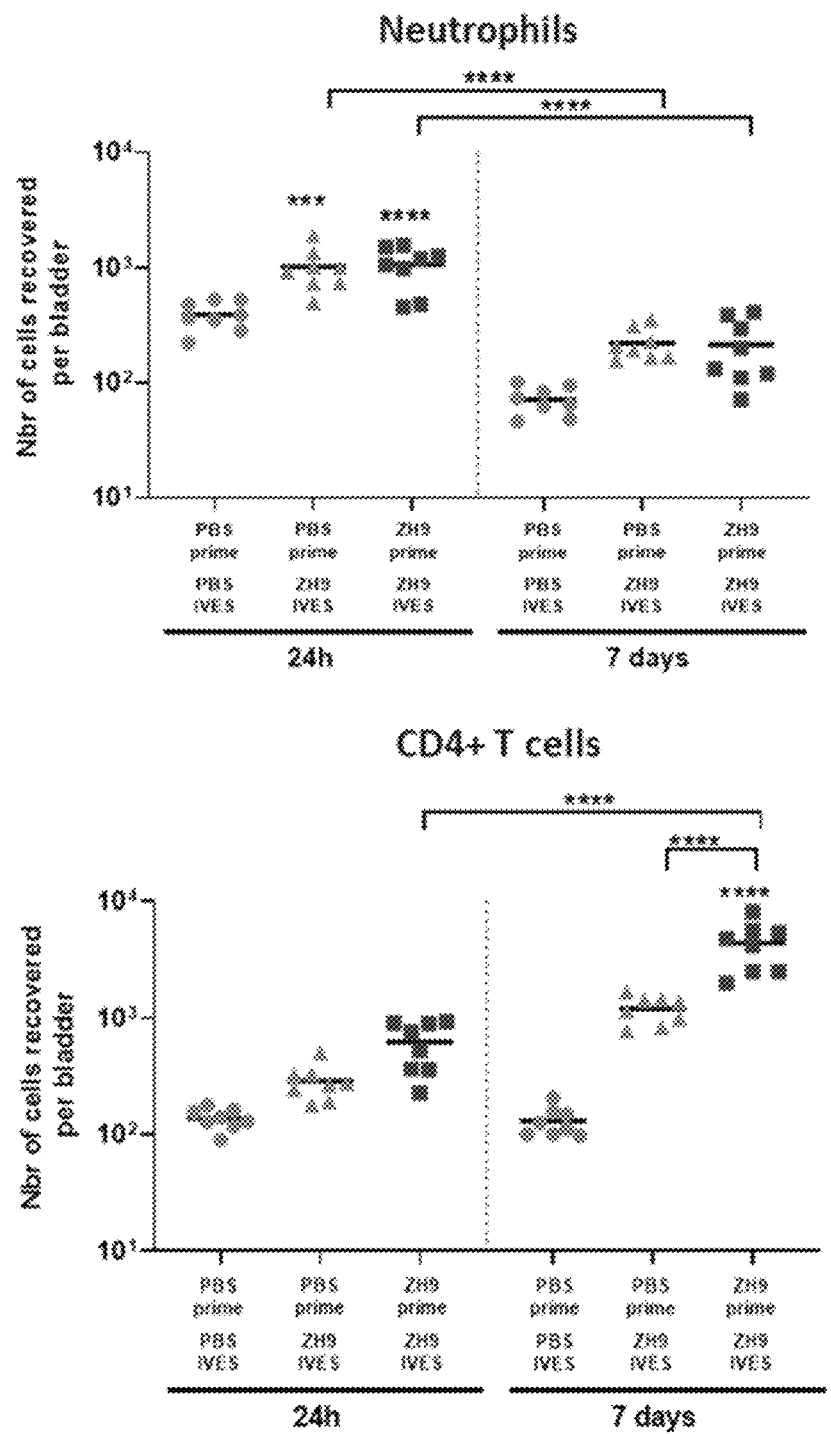
Figure 3B:
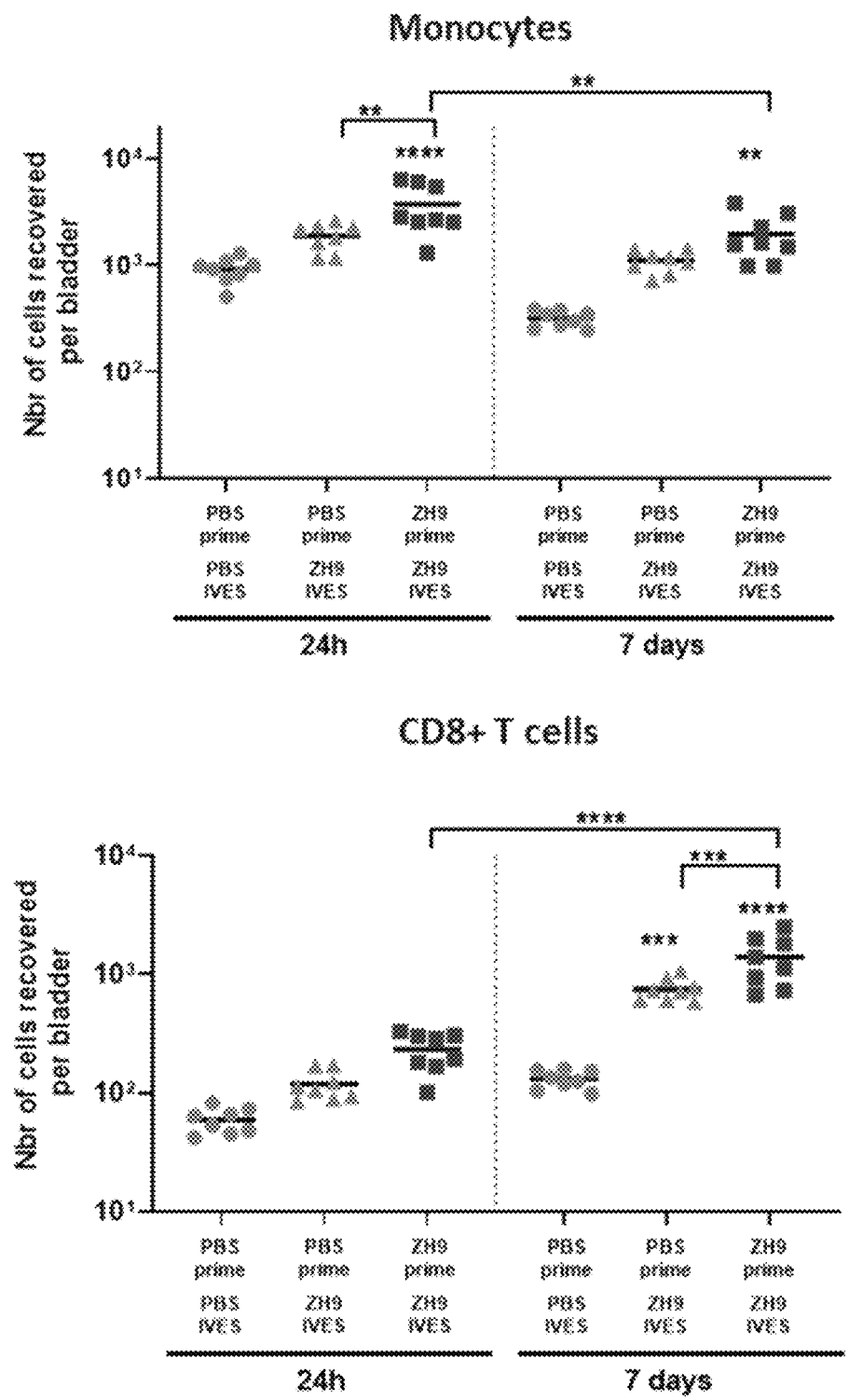
Figure 3C:
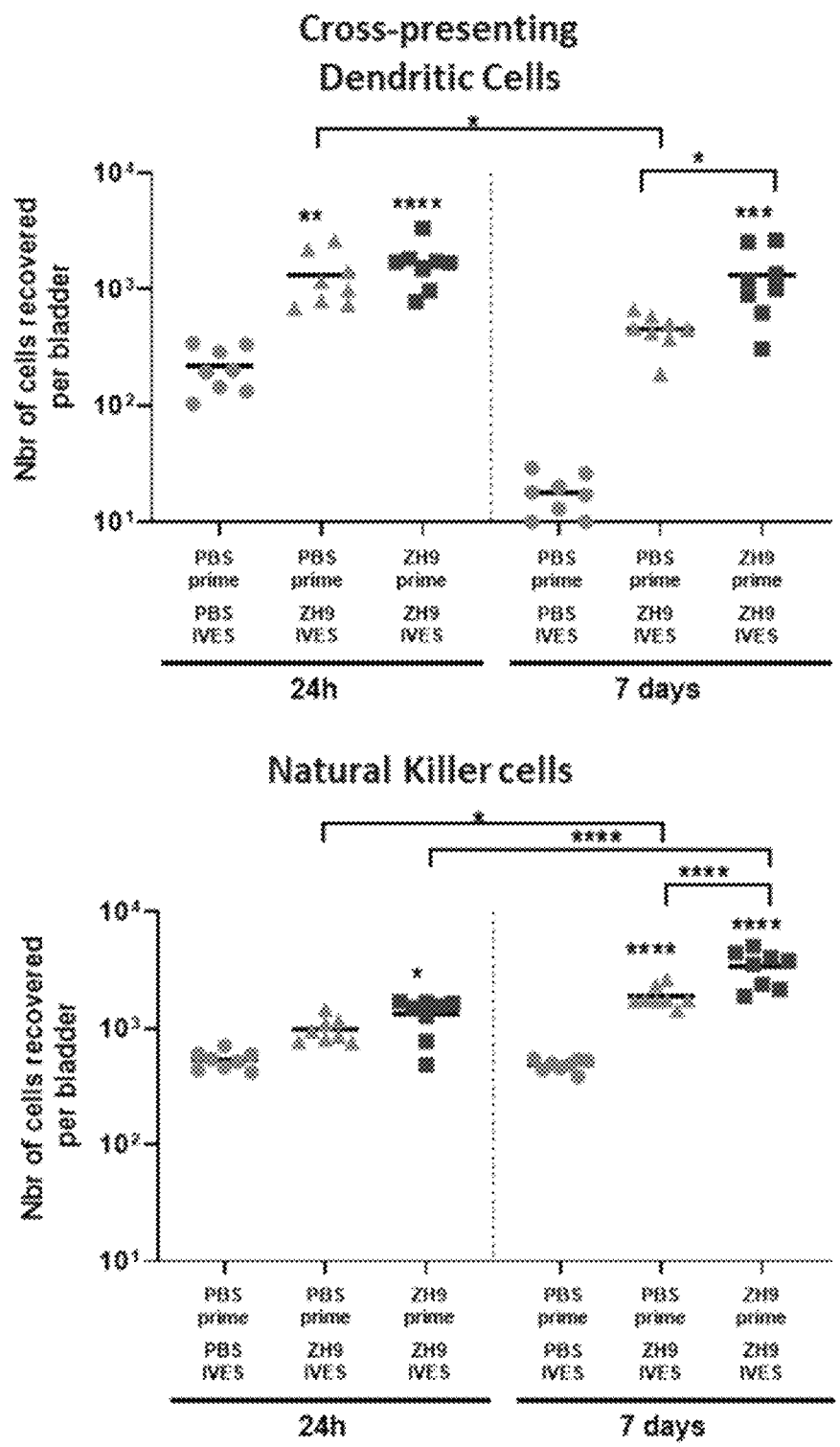

FIGS. 3A-3C show the changes 24 h and 7 days after subcutaneous systemic and local administration (ives) of *Salmonella typhi* in healthy mice in numbers of neutrophils (FIG. 3A), CD4+ T cells (FIG. 3A), monocytes (FIG. 3B), CD8+ T cells (FIG. 3B), cross-presenting dendritic cells (FIG. 3C) and natural killer cells (FIG. 3C). Individual data points represent pools of cells from n=2 (ives ZH9 treated) or n=3 (ives PBS treated) mice and 2 independent experiments of n=4 pools each, combined. Lines indicate group mean. Dendritic cell population shown defined as CD11 b+Ly6G-CD11c+Ly6C+CD103+. Statistics indicated are one-way ANOVA with Sidak's post-test.

Figure 4:
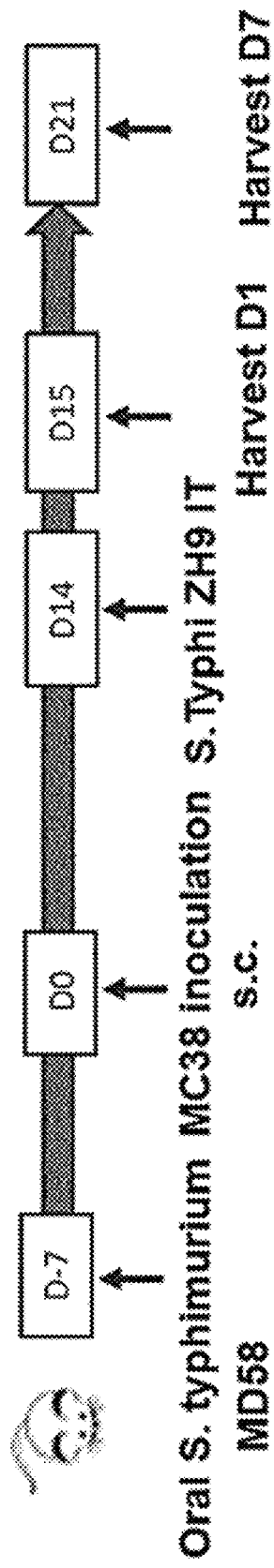

FIG. 4 shows a schematic demonstrating the timeline of oral systemic administration of *Salmonella* Typhimurium, followed by local administration (intra-tumoural) of *Salmonella typhi* in a syngeneic subcutaneous MC38 murine colon cancer model. IT, intratumoural.

Figure 5A:
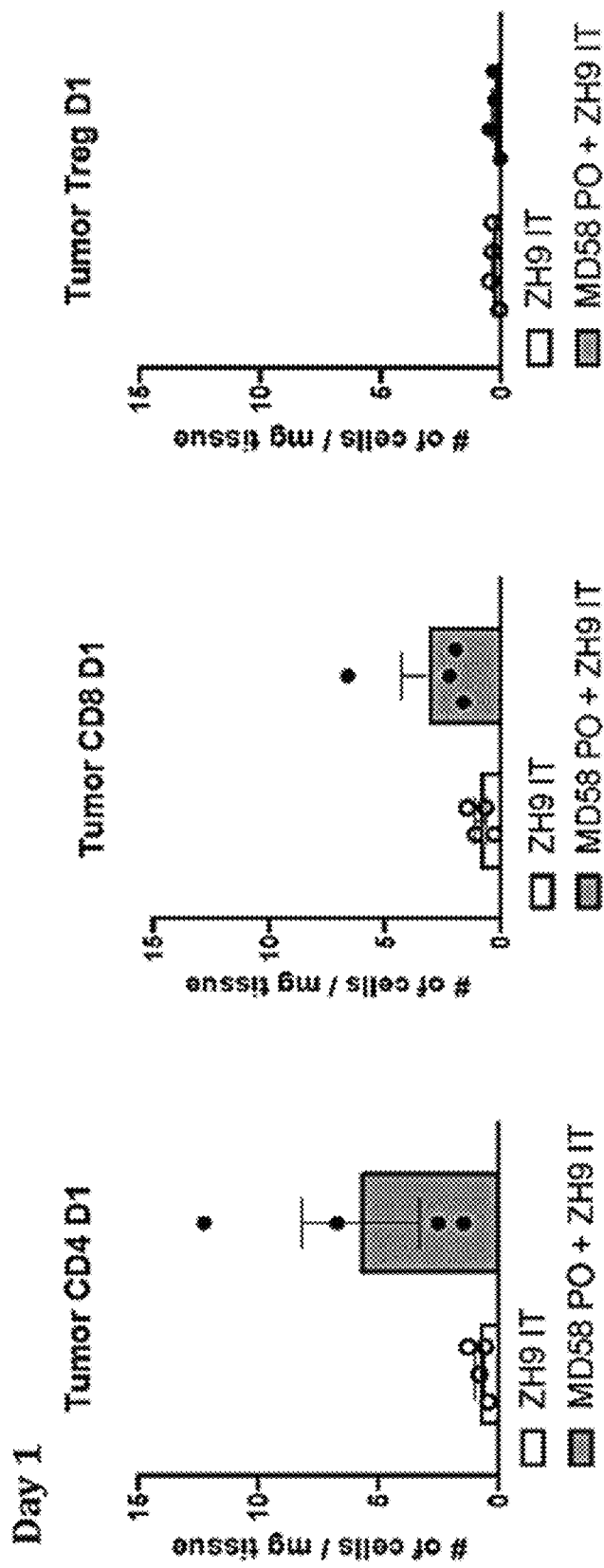
Figure 5B:
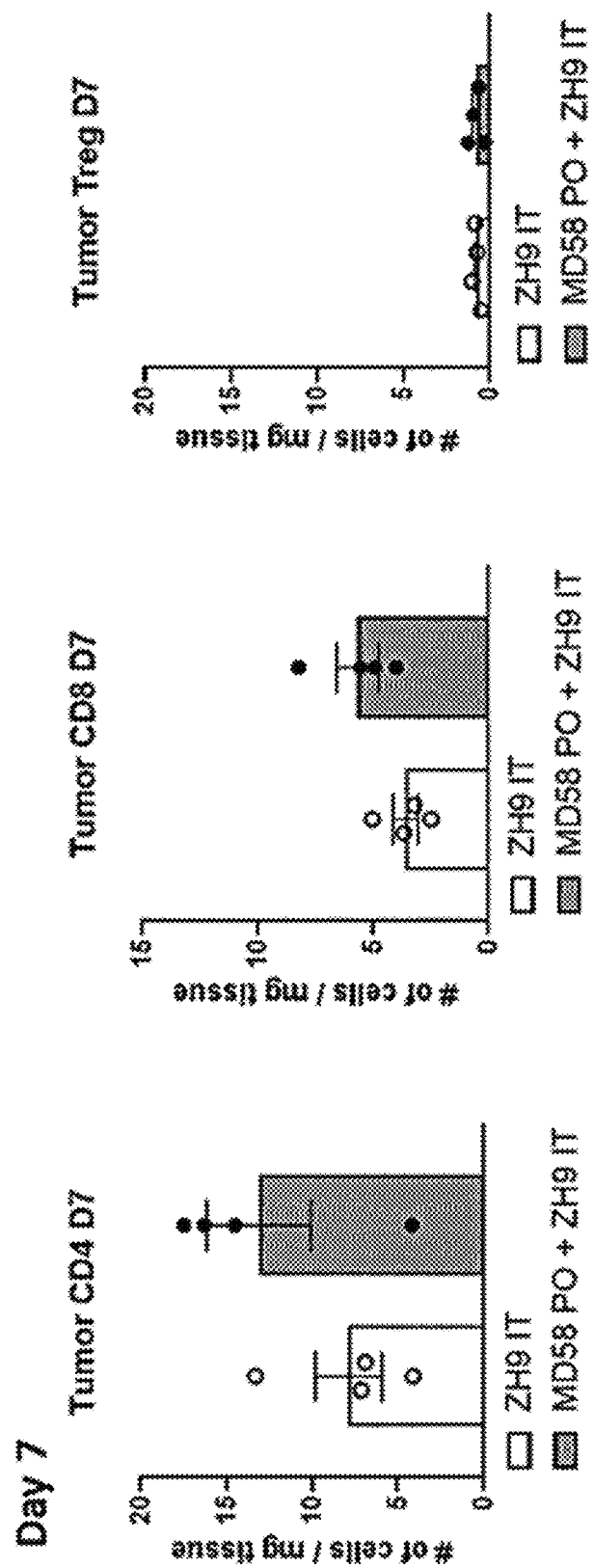

FIGS. 5A and 5B show numbers of tumour-infiltrating CD8 T cells, CD4 T cells and regulatory T cells (Treg) 1 day (FIG. 5A) and 7 days (FIG. 5B) after systemic priming with oral *Salmonella* Typhimurium in combination with intra-tumoral *Salmonella typhi* treatment as compared to intra-tumoral treatment alone. N=3 or 4 mice per group per timepoint. Bars are mean±S.E.M.

Figure 6:
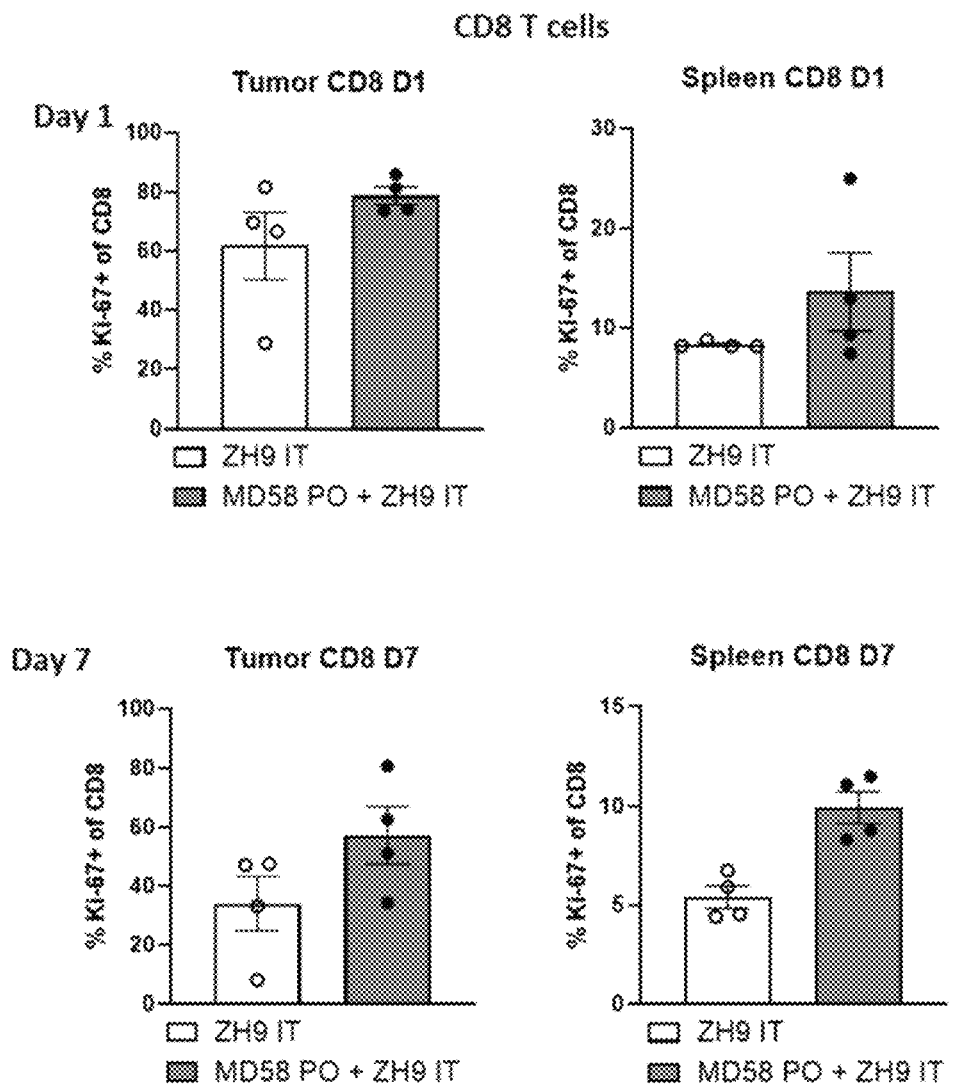

FIG. 6 shows CD8 T cell proliferation in the tumour and in the periphery 1 day and 7 days following systemic priming with oral *Salmonella* Typhimurium in combination with intra-tumoral *Salmonella typhi* treatment as compared to intra-tumoral treatment alone. N=4 mice per group per timepoint. Bars are mean±S.E.M.

Figure 7:
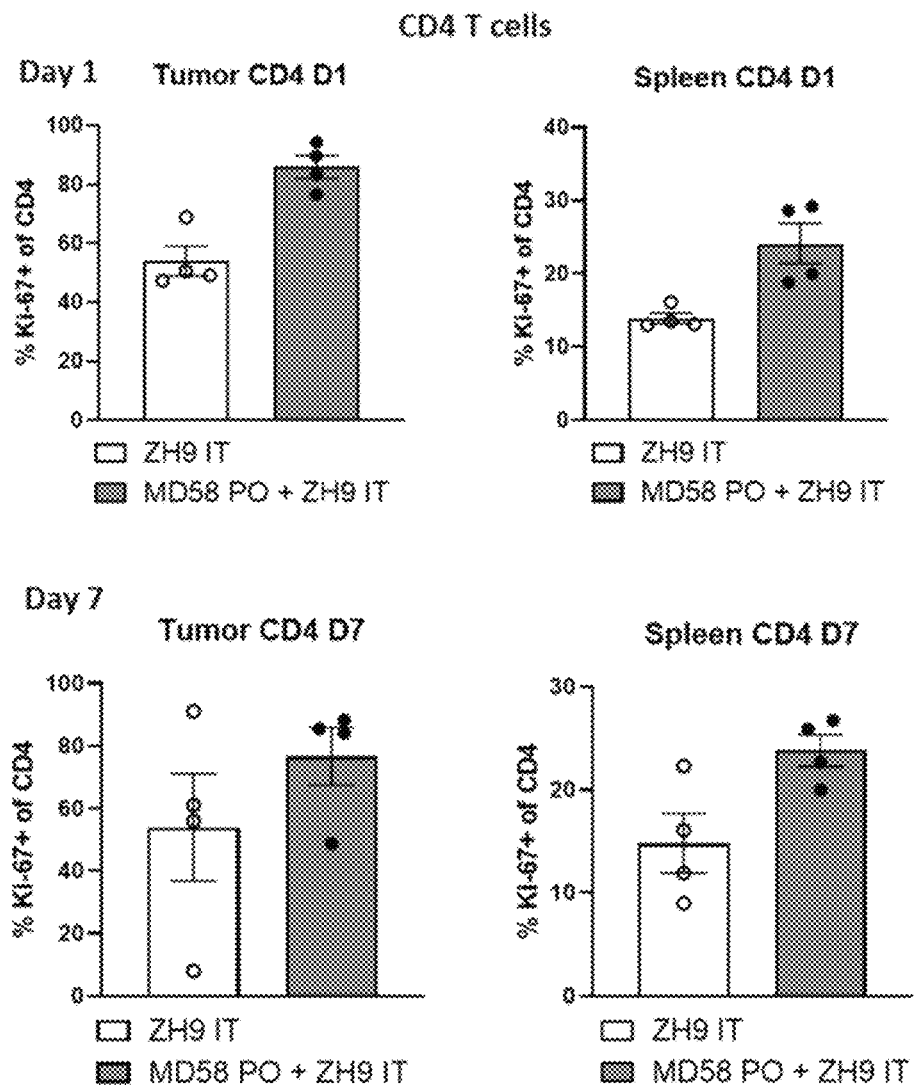

FIG. 7 shows CD4 T cell proliferation in the tumour and in the periphery 1 day and 7 days following systemic priming with oral *Salmonella* Typhimurium in combination with intra-tumoral *Salmonella typhi* treatment as compared to intra-tumoral treatment alone. N=4 mice per group per timepoint. Bars are mean±S.E.M.

Figure 8:
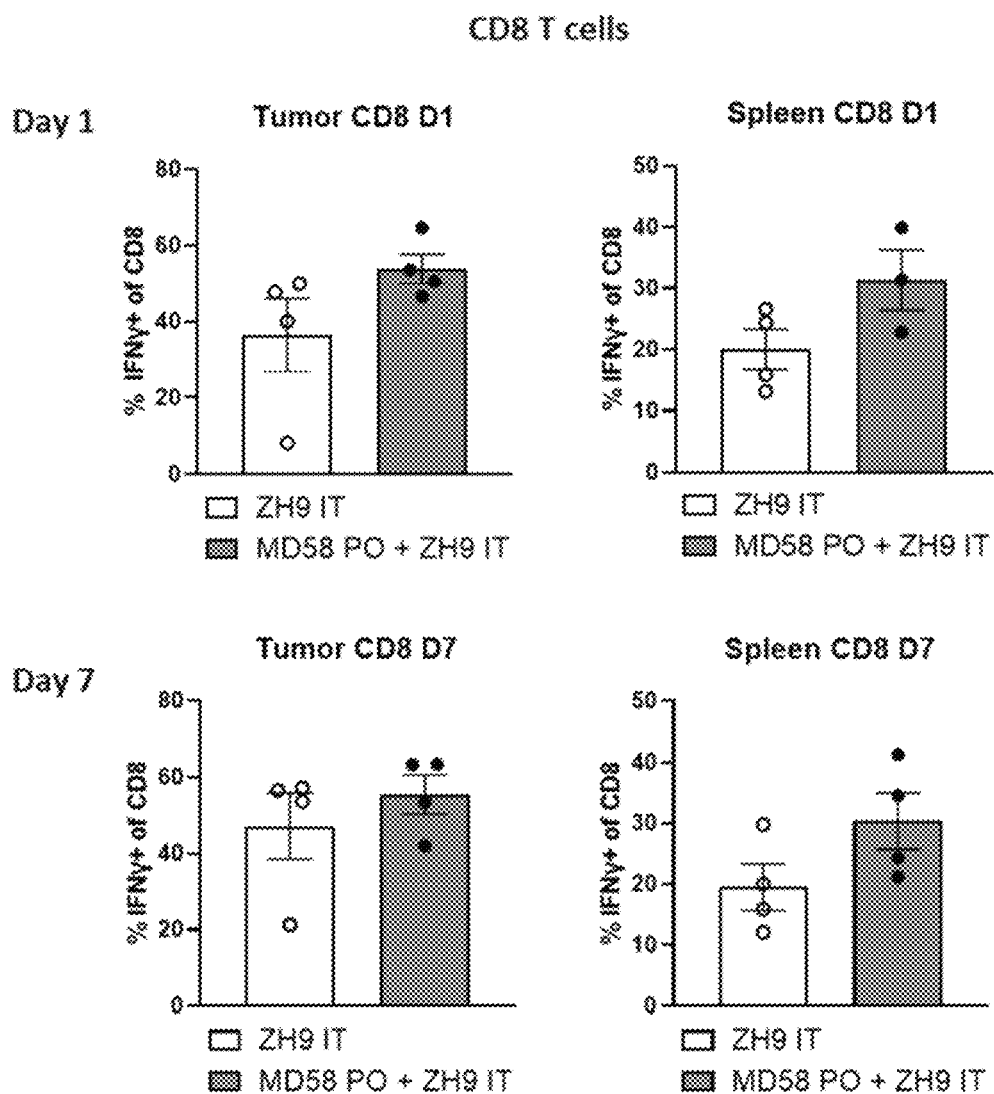

FIG. 8 shows the functional potential of CD8 T cells in mice treated with systemic priming with oral *Salmonella* Typhimurium in combination with intra-tumoral *Salmonella typhi* treatment as compared to intra-tumoral treatment alone. N=4 mice per group per timepoint. Bars are mean±S.E.M.

Figure 9:
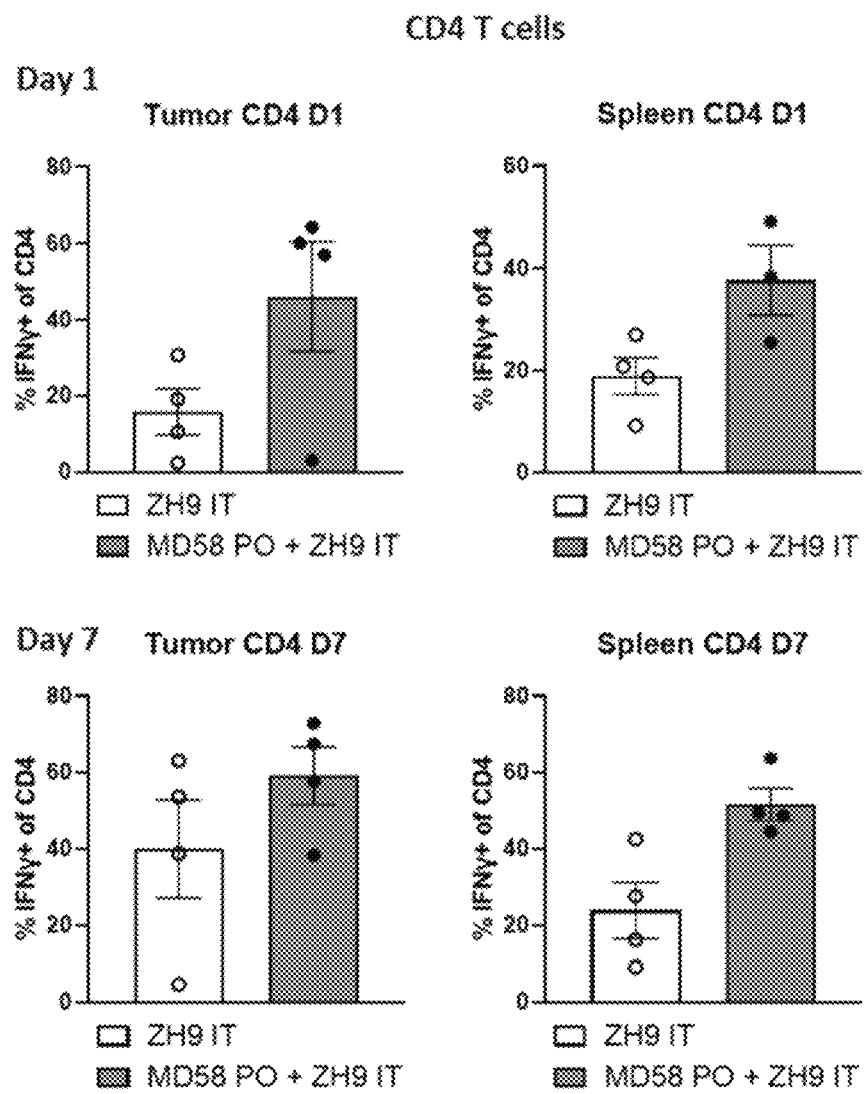

FIG. 9 shows the functional potential of CD4 T cells in mice treated with systemic priming with oral *Salmonella* Typhimurium in combination with intra-tumoral *Salmonella typhi* treatment as compared to intra-tumoral treatment alone. N=4 mice per group per timepoint. Bars are mean±S.E.M.

DETAILED DESCRIPTION

In order that the present invention may be more readily understood, certain terms are first defined. Additional definitions are set forth throughout the detailed description.

As used herein, the term "attenuated" in the context of the present invention, refers to the alteration of a microorganism to reduce its pathogenicity, rendering it harmless to the host, whilst maintaining its viability. This method is commonly used in the development of vaccines due to its ability to elicit a highly specific immune response whilst maintaining an acceptable safety profile. Development of such vaccines may involve a number of methods, examples include, but are not limited to, passing the pathogens under in vitro conditions until virulence is lost, chemical mutagenesis and genetic engineering techniques. Such an attenuated microorganism is preferably a live attenuated microorganism, although non-live attenuated microorganisms are also disclosed.

As used herein, the term "inactivating mutations" refers to modifications of the natural genetic code of a particular gene or gene promoter associated with that gene, such as modification by changing the nucleotide code or deleting sections of nucleotide or adding non-coding nucleotides or non-natural nucleotides, such that the particular gene is either not transcribed or translated appropriately or is expressed into a non-active protein such that the gene's natural function is abolished or reduced to such an extent that it is not measurable. Thus, the mutation of the gene inactivates that gene's function or the function of the protein which that gene encodes.

As used herein, the term "immunotherapy" refers to any therapy aimed at modulating immune system response, such as by antibodies or immunocytes, or by drugs or other agents that stimulate, inhibit, or otherwise modulate the immune system. These include immunomodulators, drugs or substances that affect the immune system; including but not limited to antibodies (e.g., anti-tumor antigen antibodies), epitope-binding portions of an antibody, antibody-drug conjugates including cytotoxic conjugates, radiological agents, other tumor-targeted agents, oncolytic viruses, cytokines, chemokines, interferons, interleukins, colony stimulating factors, drugs or other agents that modulate immune responses, immune cells or engineered cells that interact with, recognize, or bind to target cells.

As used herein, the term "cellular components of the immune system" refers to immunocytes such as lymphocytes, such as T and B lymphocytes, gamma-delta T cells, and NK cells, which may recognize specific antigens, such as prion, viral, bacterial, yeast, fungal, parasite, tumor-associated or tumor-specific antigens, or other antigens associated with a particular disease, disorder, or condition. Other immunocytes we refer to include white blood cells, which may be granulocytes or agranulocytes. Examples of immunocytes include neutrophils, eosinophils, basophils, lymphocytes, monocytes, and macrophages. Dendritic cells, microglia, and other antigen-presenting cells are also included within this definition.

As used herein, the term "non-natural bacterium or bacteria" refers to bacterial (prokaryotic) cells that have been genetically modified or "engineered" such that it is altered with respect to the naturally occurring cell. Such genetic modification may for example be the incorporation of additional genetic information into the cell, modification of existing genetic information or indeed deletion of existing genetic information. This may be achieved, for example, by way of transfection of a recombinant plasmid into the cell or modifications made directly to the bacterial genome. Additionally, a bacterial cell may be genetically modified by way of chemical mutagenesis, for example, to achieve attenuation, the methods of which will be well known to those skilled in the art. As such, the term "non-natural bacterium or bacteria" may refer to both recombinantly modified and non-recombinantly modified strains of bacteria.

As used herein, the term "recombinant", "recombinant strain" or "recombinant bacteria" are used interchangeably and, in the context of the present invention, refers to a strain of bacteria that has undergone genetic engineering such that the bacterial DNA has been altered by the introduction of new DNA. Recombinant DNA methods commonly involve the introduction of new DNA via a vector, for example, a plasmid. Such methods are well known to those skilled in the art. Use of recombinant strains of bacteria may confer advantageous properties to the bacterial strain, such as prolonged activity, eliciting a stronger immune response in a subject, or introduction of a desired molecule.

As used herein, the term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells.

As used herein, the terms "systemic immune response" and "systemic immunity" are used interchangeably and refers to a widespread immune response throughout the body of a subject directed against the eliciting agent, as well as widespread non-specific immune activation, as opposed to a local, spatially-restricted response. Such a response involves a complex interaction between the different cells of the immune response, for example, lymphocytes, antigen presenting cells, phagocytic cells, granulocytes and soluble macromolecules produced by the above cells or the liver, and in the context of the present invention is thought to prime the immune system of the subject, such that the subject is more responsive to the second composition comprising the live attenuated bacteria, when the second composition is administered locally to the site of the neoplastic disease. A "systemic immune response" may therefore be measured and quantified via the analysis of various different immune cell types, including, but not limited to, neutrophils, monocytes, dendritic cells, T cells (e.g. $CD4^+$ and/or $CD8^+$ T cells) and natural killer cells. The methods by which these effects can be measured are well known to those skilled in the art, for example, flow cytometry. A "systemic immune response" may also be measured and quantified by the presence of antibodies, including but not limited to IgG and IgA isotype antibodies. The methods by which these antibodies can be measured are well known to those skilled in the art, for example, ELISA. Accordingly, the first composition may act to prime (used interchangeably with "condition", "boost", "amplify", "enhance", "improve", "augment" or "promote") the immune response of a subject following administration of the second composition.

As used herein, the terms "locally" and "administered locally" are used interchangeably and in the context of the present invention refer to the way in which the second composition is administered to a subject. Accordingly, the second composition comprising live attenuated bacteria may be administered in/on/around the neoplastic disease. For example, the second composition may be administered directly to the neoplastic disease, for example, via intratumoural injection, or administered such that the second composition comes into contact with the tissue/surface of the tumour, for example intraperitoneally, intrapleurally, intravesically, peri-tumourally. The term "locally" may therefore refer to both direct and indirect contact with the neoplastic disease in question, for example, local instillation, intratumoural injection, peritumoral injection, intrapleural, intravesical and/or intraperitoneal injection. As such, the resulting immune response produced in the subject is also said to be local to the site of the neoplastic disease, that is, it is not a widespread systemic immune response, as is produced with the first composition of the invention.

The terms "tumour," "cancer", "malignancy" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumour, cancer or neoplasia to other sites, locations or regions within the subject, in which the sites, locations or regions are distinct from the primary tumour or cancer.

The terms "effective amount" or "pharmaceutically effective amount" refer to a sufficient amount of an agent to provide the desired biological or therapeutic result. That result can be reduction, amelioration, palliation, lessening, delaying, and/or alleviation of one or more of the signs, symptoms, or causes of a disease, or any other desired alteration of a biological system. In reference to cancer, an effective amount may comprise an amount sufficient to cause a tumour to shrink and/or to decrease the growth rate of the tumour (such as to suppress tumour growth) or to prevent or delay other unwanted cell proliferation. In some embodiments, an effective amount is an amount sufficient to delay development, or prolong survival or induce stabilisation of the cancer or tumour.

In some embodiments, a therapeutically effective amount is an amount sufficient to prevent or delay recurrence. A therapeutically effective amount can be administered in one or more administrations. The therapeutically effective amount of the drug or combination may result in one or more of the following: (i) reduce the number of cancer cells; (ii) reduce tumour size; (iii) inhibit, retard, slow to some extent and preferably stop cancer cell infiltration into peripheral organs; (iv) inhibit (i.e., slow to some extent and preferably stop) tumour metastasis; (v) inhibit tumour growth; (vi) prevent or delay occurrence and/or recurrence of tumour; and/or (vii) relieve to some extent one or more of the symptoms associated with the cancer.

For example, for the treatment of tumours, a "therapeutically effective dosage" may induce tumour shrinkage by at least about 5% relative to baseline measurement, such as at least about 10%, or about 20%, or about 60% or more. The baseline measurement may be derived from untreated subjects.

A therapeutically effective amount of a therapeutic compound can decrease tumour size, or otherwise ameliorate symptoms in a subject. One of ordinary skill in the art would be able to determine such amounts based on such factors as the subject's size, the severity of the subject's symptoms, and the particular composition or route of administration selected.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

As used herein, the term "subject" is intended to include human and non-human animals. Preferred subjects include human patients in need of enhancement of an immune response. The methods are particularly suitable for treating human patients having a disorder that can be treated by augmenting the immune response. In a particular embodiment, the methods are particularly suitable for treatment of cancer in vivo.

As used herein, the terms "concurrent administration" or "concurrently" or "simultaneous" mean that administration occurs on the same day. The terms "sequential administration" or "sequentially" or "separate" mean that administration occurs on different days.

"Simultaneous" administration, as defined herein, includes the administration of the first composition and the second composition within about 2 hours or about 1 hour or less of each other, even more preferably at the same time.

"Separate" administration, as defined herein, includes the administration of the first composition and the second composition, more than about 12 hours, or about 8 hours, or about 6 hours or about 4 hours or about 2 hours apart.

"Sequential" administration, as defined herein, includes the administration of the first composition and the second composition each in multiple aliquots and/or doses and/or on separate occasions. The first composition may be administered to the patient before and/or after administration of the second composition.

The use of the alternative (e.g., "or") should be understood to mean either one, both, or any combination thereof of the alternatives. As used herein, the indefinite articles "a" or "an" should be understood to refer to "one or more" of any recited or enumerated component.

As used herein, "about" means within an acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" can mean a range of up to 20%. When particular values are provided in the application and claims, unless otherwise stated, the meaning of "about" should be assumed to be within an acceptable error range for that particular value.

The present invention provides for an effective way in which a neoplastic disease in a subject may be prevented and/or treated by the use of multiple doses (i.e., at least two doses) of live attenuated bacteria, wherein the doses are administered via distinct routes of administration to effectively activate the immune system of a subject against a neoplastic disease.

Accordingly, in a first aspect the present invention provides for a first composition comprising a live attenuated bacterium for use in the treatment, prevention, reduction, inhibition, prevention of recurrence, or control of a neoplastic disease in a subject being or intended to be administered a second composition comprising a live attenuated bacterium, said bacterium being the same or different to that of the first composition, wherein the first composition is formulated for oral, intravenous, intranasal or subcutaneous delivery to stimulate a systemic immune response in the subject and is for administration simultaneously, separately or sequentially with the second composition, and wherein the second composition is for administration locally to the site of the neoplastic disease.

It is therefore envisaged that the live attenuated bacterium of the first composition acts as a "priming" agent of a subject's immune system, resulting in a systemic immune response and the subsequent ability of the subject's immune system to be able to mount a more effective innate immune response as well as an effective adaptive response to a neoplastic disease when further locally administered the live attenuated bacterium of the second composition.

The first composition comprising the live attenuated bacteria is formulated for oral, intravenous, intranasal, intradermal or subcutaneous delivery. Formulations suitable for these routes of delivery will be apparent to the skilled person. The first composition may preferentially be a liquid frozen formulation or lyophilised by a process such as freeze-drying and stored appropriately, for example, in sachets, for later rehydration and administration. Alternatively, the first composition may be dispensed into enterically coated capsules. For the encapsulated formulation, the lyophilised first composition is preferably mixed with a bile-adsorbing resin, such as cholestyramine, to enhance survival when released from the capsule into the small intestine (for further details, see WO 2010/079343). The particular formulation of the first composition may vary depending on a variety of factors, for example, the route of administration or the target patient population i.e., young children, adolescents or adults. The first composition may also be formulated to comprise any other suitable adjuvant, diluent or excipient. Suitable adjuvants, diluents or excipients include, but are not limited to, disodium hydrogen phosphate, soya peptone, potassium dihydrogen phosphate, ammonium chloride, sodium chloride, magnesium sulphate, calcium chloride, sucrose, sterile saline, and sterile water.

It is envisaged that any live attenuated bacteria, or combination of live attenuated bacteria, capable of producing the required immune response in a subject may be used in the present invention. In a preferred embodiment, the live attenuated bacterium of the first and/or second composition may be a gram-negative bacterium. Examples of gram-negative bacteria for use in the present invention include, but are not limited to, *Escherichia coli, Salmonella, Shigella, Pseudomonas, Moraxella, Helicobacter, Stenotrophomonas, Bdellovibrio, Legionella, Chlamydia* and *Yersinia*. Gram-negative bacteria can be readily identified and differentiated from gram-positive bacteria via Gram's differential staining technique, where gram-negative bacteria do not retain the crystal violet stain.

Preferably, the live attenuated bacteria of the first and/or second composition may be a *Salmonella* spp. Examples of *Salmonella* species for use in the present invention are *Salmonella enterica* and *Salmonella bongori*. *Salmonella enterica* can be further sub-divided into different serotypes or serovars. Examples of said serotypes or serovars for use in the present invention are *Salmonella enterica Typhi, Salmonella enterica* Paratyphi A, *Salmonella enterica* Paratyphi B, *Salmonella enterica* Paratyphi C, *Salmonella enterica* Typhimurium and *Salmonella enterica* Enteritidis. In a preferred embodiment, the live attenuated bacterium may be *Salmonella enterica* serovar *typhi* and/or *Salmonella enterica* Typhimurium.

The live attenuated bacteria of the first and second composition may be the same live attenuated bacteria or different live attenuated bacteria. Accordingly, various different combinations of live attenuated bacterium in accordance with the present invention are herein disclosed. In a preferred embodiment, the live attenuated bacteria of the first and second composition are of the same species. In a most preferred embodiment, the live attenuated bacteria of the first and second composition are both of the *Salmonella enterica* species.

The live attenuated bacterium of the first composition and the live attenuated bacterium of the second composition may comprise a genetically modified non-natural bacterium. As would be understood by a person of skill in the art, genes may be mutated by a number of well-known methods in the art, such as homologous recombination with recombinant plasmids targeted to the gene of interest, in which case an engineered gene with homology to the target gene is incorporated into an appropriate nucleic acid vector (such as a plasmid or a bacteriophage), which is transfected into the target cell. The homologous engineered gene is then recombined with the natural gene to either replace or mutate it to achieve the desired inactivated mutation. Such modification may be in the coding part of the gene or any regulatory portions, such as the promoter region. As would be understood by a person of skill in the art, any appropriate genetic modification technique may be used to mutate the genes of interest, such as the CRISPR/Cas system, e.g., CRISPR/Cas 9.

Thus, numerous methods and techniques for genetically engineering bacterial strains will be well known to the person skilled in the art. These techniques include those required for introducing heterologous genes into the bacteria either via chromosomal integration or via the introduction of a stable autosomal self-replicating genetic element. Exemplary methods for genetically modifying (also referred to as "transforming" or "engineering") bacterial cells include bacteriophage infection, transduction, conjugation, lipofection or electroporation. A general discussion on these and other methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); which are hereby incorporated by reference.

Accordingly, both the first composition and second composition may comprise bacteria that has had its genetic make-up altered in some form, for example, via genetic engineering, or via chemical mutagenesis, to induce a change, for example, a mutation, an addition or deletion. The first composition and/or second composition may be genetically modified such that the first composition and second composition comprise a recombinant strain of bacteria. Alternatively, the first composition and/or second composition may comprise a non-recombinant strain of bacteria. The first composition and second composition may comprise the same live attenuated bacteria that has been genetically modified as described above, or the first and second composition may comprise two different bacterial strains (may or may not be within the same genus) that have been genetically modified. Alternatively, the first composition may comprise a recombinant strain of bacteria and the second composition may comprise a non-recombinant strain of bacteria and vice versa.

It is envisaged that any bacteria capable of inducing the systemic immune response of a subject in accordance with the invention may be used. Accordingly, any live attenuated bacteria capable of inducing a systemic immune response as part of the first composition is herein disclosed, and any live attenuated bacteria that induces a local immune response as part of the second composition is herein disclosed. In a preferred embodiment, any attenuated, non-pathogenic, *Salmonella enterica* serovar *Typhi* or Typhimurium strain may be used. In a further preferred embodiment, the live attenuated bacterium of the first or second composition may be selected from the group comprising Ty21a, CVD 908-htrA, CVD 909, Ty800, ZH9 (also referred to as "M01ZH09"), ZH9PA, x9633, x639, x9640, x8444, DTY88, MD58, WT05, ZH26, SL7838, SL7207, VNP20009, A1-R, or any combinations thereof. The live attenuated bacteria of the first and second composition may be the same, for example both the first and second composition may comprise Ty21a, CVD 908-htrA, CVD 909, Ty800, ZH9, ZH9PA, x9633, x639, x9640, x8444, DTY88, MD58, WT05, ZH26, SL7838, SL7207, VNP20009 or A1-R. Alternatively, the live attenuated bacteria of the first and second composition may be different, for example, the first composition may be Ty21a and the second composition may be CVD 908-htrA, CVD 909, Ty800, ZH9, ZH9PA, x9633, x639, x9640, x8444, DTY88, MD58, WT05, ZH26, SL7838, SL7207, VNP20009 or A1-R, and so on. In a preferred embodiment, the live attenuated bacteria of at least one of the first or second composition is *Salmonella typhi* ZH9. For example, the live attenuated bacteria of the first composition may be *Salmonella* Typhimurium MD58 and the live attenuated bacteria of the second composition may be *Salmonella typhi* ZH9. In a further preferred embodiment, the live attenuated bacteria of the first and second composition are the same. In a most preferred embodiment, the live attenuated bacteria of the first and second composition are both *Salmonella typhi* ZH9.

Accordingly, wherein the first and/or second composition comprise a genetically modified non-natural bacterium, it is preferred that said genetically modified non-natural bacteria is derived from *Salmonella* spp. It is further preferred that said *Salmonella* spp. may comprise an attenuating mutation in a *Salmonella* Pathogenicity Island 2 (SPI-2) gene and/or an attenuating mutation in a second gene. Preferably, the genetically modified non-natural bacteria is derived from *Salmonella* spp. and comprises both an attenuating mutation in a SPI-2 gene and an attenuating mutation in a second gene. Suitable genes and details of such a live attenuated *Salmonella* microorganism is as described in WO 2000/68261, which is hereby incorporated by reference in its entirety.

The SPI-2 gene may be an ssa gene. For example, the invention includes an attenuating mutation in one or more of ssaV, ssaJ, ssaU, ssaK, ssaL, ssaM, ssaO, ssaP, ssaQ, ssaR, ssaS, ssaT, ssaD, ssaE, ssaG, ssaI, ssaC and ssaH. Preferably, the attenuating mutation is in the ssaV or ssaJ gene. Even more preferably, the attenuating mutation is in the ssaV gene.

The genetically engineered *Salmonella* microorganism may also comprise an attenuating mutation in a second gene, which may or may not be in the SPI-2 region. The mutation may be outside of the SPI-2 region and involved in the biosynthesis of aromatic compound. For example, the invention may include an attenuating mutation in an aro gene. In a preferred embodiment, the aro gene is aroA or aroC. Even more preferably, the aro gene is aroC.

When the genetically engineered *Salmonella* microorganism comprises a double attenuating mutation, both mutations may be in the SPI-2 gene or both mutations may be in a second gene, which may or may not be in the SPI-2 region. Preferably, the genetically engineered *Salmonella* microorganism comprises an attenuating mutation in the ssaV gene and an aro gene, even more preferably, wherein the aro gene is aroC.

The genetically engineered microorganism may further comprise one or more gene cassettes. Such gene cassettes may be used to deliver additional molecules to support the function of the genetically modified non-natural bacterium as an immune system primer and/or stimulator.

In yet another embodiment, the genetically engineered microorganism may be derived from a *Salmonella* microorganism and may comprise inactivating mutations in one or more genes selected from pltA, pltB, cdtB and ttsA and further comprises attenuating mutations in one or more genes selected from aroA and/or aroC and/or ssaV. Preferably, the attenuating mutations are in aroC and ssaV. Details of said genes and mutations are as described in WO 2019/110819, which is hereby incorporated by reference in its entirety.

The present invention provides for a first and second composition comprising the live attenuated bacteria herein disclosed that can be used for the prevention and/or treatment of neoplastic disease, and/or secondary diseases associated with neoplastic disease. In one embodiment, the neoplastic disease may be a solid cancer and/or a haematological malignancy. Neoplasia, tumours and cancers include benign, malignant, metastatic and non-metastatic types, and include any stage (I, II, III, IV or V) or grade (G1, G2, G3, etc.) of neoplasia, tumour, or cancer, or a neoplasia, tumour, cancer or metastasis that is progressing, worsening, stabilized or in remission.

Cancers that may be treated according to the invention include, but are not limited to, cells or neoplasms of the bladder, blood, bone, bone marrow, brain, breast, colon, esophagus, gastrointestines, gum, head, kidney, liver, lung, nasopharynx, neck, ovary, prostate, skin, stomach, testis, tongue, or uterus. In addition, the cancer may specifically be of the following histological type, though it is not limited to the following: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumour, malignant; bronchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma with squamous metaplasia; thymoma, malignant; ovarian stromal tumour, malignant; thecoma, malignant; granulosa cell tumour, malignant; androblastoma, malignant; Sertoli cell carcinoma; Leydig cell tumour, malignant; lipid cell tumour, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumour; Mullerian mixed tumour; nephroblastoma; hepatoblastoma; carcinosarcoma; mesenchymoma, malignant; Brenner tumour, malignant; phyllodes tumour, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumour of bone; Ewing's sarcoma; odontogenic tumour, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumour; meningioma, malignant; neurofibrosarcoma; neurilemmoma, malignant; granular cell tumour, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Preferably, the solid cancer and/or the haematological malignancy may be a cancer selected from prostate cancer, oesophageal cancer, liver cancer, renal cancer, lung cancer, breast cancer, colorectal cancer, bladder cancer, breast cancer, pancreatic cancer, brain cancer, hepatocellular cancer, lymphoma, leukaemia, gastric cancer, cervical cancer, ovarian cancer, mesothelioma, thyroid cancer, melanoma, carcinoma, head and neck cancer, skin cancer or sarcoma. Even more preferably, the neoplastic disease may be associated with a cancer selected from bladder cancer, lung cancer, mesothelioma, hepatocellular cancer melanoma, oesophageal cancer, gastric cancer, ovarian cancer, colorectal cancer, head and neck cancer or breast cancer. In a preferred embodiment, the neoplastic disease is colorectal cancer or bladder cancer. In a most preferred embodiment, the neoplastic disease is bladder cancer.

Where the neoplastic disease to be prevented and/or treated is bladder cancer, the bladder cancer may be a non-muscle invasive bladder cancer, or a muscle invasive bladder cancer. Non-muscle invasive bladder cancer is defined as any bladder cancer consisting of cancerous cells that are contained inside the lining of the bladder and is the most common type. Muscle invasive bladder cancer is defined as any bladder cancer in which the cancerous cells have spread beyond the lining of the bladder and have therefore infiltrated into the surrounding bladder muscle. The latter is less common but has a higher chance of spreading to other parts of the body.

Where the bladder cancer is a non-muscle invasive bladder cancer, said bladder cancer may be referred to as a transitional cell (urothelial) carcinoma (TCC). TCC accounts for approximately 95% of bladder cancers, accordingly, the live attenuated bacteria of the first and second composition of the present invention may preferably be used for the prevention and/or treatment of TCC. TCC may be further divided into two subtypes of bladder cancer: papillary carcinoma and flat carcinomas. Accordingly, in yet a further embodiment, the live attenuated bacteria of the first and second composition of the present invention may preferably be used for the prevention and/or treatment of a papillary carcinoma and/or a flat carcinoma. Alternative bladder cancers that the present invention may also be suitable for include, but are not limited to, squamous cell carcinoma, adenocarcinoma, small-cell carcinoma and/or sarcoma.

In one embodiment, the present invention provides for a first composition comprising a live attenuated bacterium for use in the treatment, reduction, inhibition, prevention of recurrence, or control of a neoplastic disease in a subject being or intended to be administered a second composition comprising a live attenuated bacterium, wherein the first composition is formulated for oral delivery to stimulate a systemic immune response in the subject and is for administration simultaneously, separately or sequentially with the second composition, wherein the second composition is for administration locally to the site of the neoplastic disease, and wherein the live attenuated bacterium of the first and second composition is the *Salmonella* serovar *typhi* ZH9 strain.

In a further embodiment, the present invention provides for a first composition comprising a live attenuated bacterium for use in the treatment, reduction, inhibition, prevention of recurrence, or control of bladder cancer in a subject being or intended to be administered a second composition comprising a live attenuated bacterium, wherein the first composition is formulated for oral delivery to stimulate a systemic immune response in the subject and is for administration simultaneously, separately or sequentially with the second composition, wherein the second composition is for administration locally to the bladder, and wherein the live attenuated bacterium of the first and second composition is the *Salmonella* serovar *typhi* ZH9 strain.

In another embodiment, the present invention provides for a first composition comprising a live attenuated bacterium for use in the treatment, reduction, inhibition, prevention of recurrence, or control of TCC in a subject being or intended to be administered a second composition comprising a live attenuated bacterium, wherein the first composition is formulated for oral delivery to stimulate a systemic immune response in the subject and is for administration simultaneously, separately or sequentially with the second composition, wherein the second composition is for administration locally to the bladder, and wherein the live attenuated bacterium of the first and second composition is the *Salmonella* serovar *typhi* ZH9 strain.

In another embodiment, the present invention provides for a first composition comprising a live attenuated bacterium for use in the treatment, reduction, inhibition, prevention of recurrence, or control of a neoplastic disease in a subject being or intended to be administered a second composition comprising a live attenuated bacterium, wherein the first composition is formulated for subcutaneous delivery to stimulate a systemic immune response in the subject and is for administration simultaneously, separately or sequentially with the second composition, wherein the second composition is for intravesical administration to the site of the neoplastic disease, and wherein the live attenuated bacterium of the first and second composition is the *Salmonella* serovar *typhi* ZH9 strain.

In another embodiment, the present invention provides for a first composition comprising a live attenuated bacterium for use in the treatment, reduction, inhibition, prevention of recurrence, or control of bladder cancer in a subject being or intended to be administered a second composition comprising a live attenuated bacterium, wherein the first composition is formulated for subcutaneous delivery to stimulate a systemic immune response in the subject and is for administration simultaneously, separately or sequentially with the second composition, wherein the second composition is for intravesical administration to the bladder, and wherein the live attenuated bacterium of the first and second composition is the *Salmonella* serovar *typhi* ZH9 strain.

In another embodiment, the present invention provides for a first composition comprising a live attenuated bacterium for use in the treatment, reduction, inhibition, prevention of recurrence, or control of a neoplastic disease in a subject being or intended to be administered a second composition comprising a live attenuated bacterium, wherein the first composition is formulated for oral delivery to stimulate a systemic immune response in the subject and is for administration simultaneously, separately or sequentially with the second composition, wherein the second composition is for intratumoural administration to the site of the neoplastic disease, wherein the live attenuated bacterium of the first composition is the *Salmonella* serovar Typhimurium MD58 strain and the live attenuated bacterium of the second composition is the *Salmonella* serovar *typhi* ZH9 strain.

In another embodiment, the present invention provides for a first composition comprising a live attenuated bacterium for use in the treatment, reduction, inhibition, prevention of recurrence, or control of colorectal cancer in a subject being or intended to be administered a second composition comprising a live attenuated bacterium, wherein the first composition is formulated for oral delivery to stimulate a systemic immune response in the subject and is for administration simultaneously, separately or sequentially with the second composition, wherein the second composition is for intratumoural administration to the site of the colorectal cancer, wherein the live attenuated bacterium of the first composition is the *Salmonella* serovar Typhimurium MD58 strain and the live attenuated bacterium of the second composition is the *Salmonella* serovar *typhi* ZH9 strain.

It is envisaged that the different delivery routes of the first and second compositions, i.e., the first being administered orally, intravenously, intranasally, intrapleuraly, intradermally or subcutaneously to achieve a systemic effect and the second one being administered locally to the site of the neoplastic disease, complement each other in such a way that a neoplastic disease in a subject may be effectively prevented and/or treated. Specifically, such a combination activates the immune system's anti-tumour activity in a subject in a more specific, targeted and effective way than if each of the first or second compositions was given in isolation.

As described above, the second composition is for local administration to the site of a neoplastic disease in a subject, for example, the bladder. Accordingly, the second composition may be administered in any form in which the second composition is considered to be within close proximity of the neoplastic disease. As used herein, the term "close proximity" is intended to refer to the area or region surrounding the neoplastic disease out to a distance. For example, in one embodiment the term "close proximity" may refer to the area/region extending up to 10 mm from the boundary of the neoplastic disease. In another embodiment, the term "close proximity" may refer to the area/region extending up to 5 mm from the boundary of the neoplastic disease. In yet another embodiment, the term "close proximity" may refer to the area/region extending up to 2.5 mm from the boundary of the neoplastic disease. The distance at which the second composition is administered from the site of the neoplastic disease will allow for the biological effects of the second composition, for example, recruitment and activation of various immune cell types, to have an effect on the neoplastic disease in question, whilst having minimal/no effect on tissue situated in unrelated areas of the body. As such, the second composition may be administered directly to the neoplastic tissue, or to surrounding tissue in close proximity of the neoplastic disease. Additionally, the second composition may be administered "in" or "on" the neoplastic tissue or surrounding tissue. As such, the term "local administration" refers to any context in which the live attenuated bacteria may come into contact with the neoplastic disease or into contact with the immediately surrounding tissue to have the desired effect.

Preferably, the second composition may be administered via local instillation, intra-peritoneally, intrapleurally, intravesically, peritumoral injection or intratumoural injection, wherein "instillation" refers to the second composition being introduced into the relevant anatomical site and remaining there for a specific amount of time before being drained, voided or withdrawn, "intra-peritoneally" refers to an injection of the second composition into the peritoneum of the subject, "intrapleurally" refers to an injection of the second composition into the pleura, or a pleural cavity, of the subject, "intravesically" refers to an injection or instillation via a catheter into the urinary bladder, "peritumoral injection" refers to an injection of the second composition around the site of the neoplastic disease, and "intratumoural injection" refers to an injection of the second composition directly into the neoplastic disease of the subject. It is understood that the specific method of administration of the second composition may depend on the neoplastic disease to be treated, for example, both the location and type of neoplastic disease to be treated. For example, if it is desirable that a large surface area of a body cavity is treated, for example, a pleural cavity of a subject, then administration via instillation may be most appropriate. Alternatively, if the neoplastic disease is located within the peritoneal cavity, for example, ovarian cancer, administration via intraperitoneal injection may be most appropriate. Yet further, if the neoplastic disease to be prevented and/or treated is a haematological malignancy, it is noted that intra-tumoural injection may not be the method of administration of choice.

In the instance where the neoplastic disease to be prevented and/or treated is bladder cancer, it is preferable that the second composition may be administered via intravesical instillation, also referred to as bladder instillation, intravesical treatment or intravesical therapy. Such a method of administration refers to the way in which the second composition may be delivered to the urinary bladder via a catheter. As previously described, such a method is considered to be "local" due to the reduced systemic side effects compared with oral or parenteral delivery.

Accordingly in one embodiment, the present invention provides for a first composition comprising a live attenuated bacterium for use in the treatment, reduction, inhibition, prevention of recurrence, or control of bladder cancer in a subject being or intended to be administered a second composition comprising a live attenuated bacterium, said bacterium being the same or different to that of the first composition, wherein the first composition is formulated for oral or subcutaneous delivery to stimulate a systemic immune response in the subject and is for administration simultaneously, separately or sequentially with the second composition, wherein the second composition is for administration via intravesical instillation.

In another embodiment, the present invention provides for a first composition comprising a live attenuated bacterium for use in the treatment, reduction, inhibition, prevention of recurrence, or control of bladder cancer in a subject being or intended to be administered a second composition comprising a live attenuated bacterium, wherein the first composition is formulated for oral or subcutaneous delivery to stimulate a systemic immune response in the subject and is for administration simultaneously, separately or sequentially with the second composition, wherein the second composition is for administration via intravesical instillation, and wherein the live attenuated bacterium of the first and second composition is the *Salmonella* serovar *typhi* ZH9 strain.

The first composition of the present invention is intended to produce a systemic immune response in a subject. Accordingly, the first composition of the present invention may be a vaccine or vaccine composition. Such terms are used interchangeably and refer to a biological preparation in which the subject produces an immune response to said biological preparation, therefore providing active acquired immunity to a particular infectious disease, for example, a disease caused by a *Salmonella* spp. In the context of the present invention, the vaccine may contain an agent, or "foreign" agent, that resembles the infection-causing bacteria, which is a weakened or killed form of said bacteria, or any portion of, or fragment of, a bacteria protein, capsule, DNA or RNA. Such a foreign agent would be recognised by a vaccine-receiver's immune system, which in turn would destroy said agent and develop "memory" against the bacteria, inducing a level of lasting protection against future bacterial infections from the same or similar viruses. Through the route of vaccination, including those vaccine compositions of the present invention, it is envisaged that once the vaccinated subject again encounters the same bacteria or bacterial isolate of which said subject was vaccinated against, the individual's immune system may thereby recognise said bacteria or bacterial isolate and elicit a more effective defence against infection. The active acquired immunity that is induced in the subject as a result of the vaccine may be humoral and/or cellular in nature. Accordingly, in the embodiment wherein the first and second composition are the same, the first composition of the present invention may not only induce a systemic immune response that boosts the non-specific innate immune response to the second composition, but may also confer the additional benefit of the subject acquiring active immunity to the live attenuated bacteria of the first composition.

The first composition may be administered simultaneously, separately or sequentially with the second composition to a subject in need thereof. Without being bound by theory, it is thought that the administration of the first composition prior to that of the second composition allows for the immune system of the subject to be effectively primed prior to the administration of the second composition, therefore resulting in a more effective prevention or treatment strategy. Accordingly, whilst there may be some instances in which the first and second composition are administered within quick succession of one another, or at the same time, it is preferred that the live attenuated bacterium of the first composition is administered to the subject prior to the live attenuated bacterium of the second composition.

The amount of the live attenuated bacteria of the first composition administered to the subject is sufficient to elicit a systemic immune response in the subject, so that the subject's immune system is effectively primed to receive the second composition at a site local to the neoplastic disease, resulting in the subject's immune system being able to mount an effective immune response to the cancer or tumour when treated with the two compositions in combination. The immune response initiated by the administration of the composition may be of a therapeutic level in itself or be of a sub-therapeutic level requiring the subsequent administration of second composition to exert a therapeutic effect.

It is envisaged that the first and second compositions comprising the live attenuated bacteria may be administered at least once or at least twice, two weeks apart. The first composition may be administered before, during or after administration of the second composition. Preferably, at least one administration of the first composition would occur prior to the administration of the second composition, such administration may occur at least one week prior to the administration of the second composition. It is envisaged that the administration of the first and second composition may be repeated, depending on the treatment regimen. The live attenuated bacteria of the first and/or second composition may be administered at a dose of between $10^4$ and $10^{12}$ CFU, where CFU is a colony-forming unit. For example, suitable doses may be between $10^4$ and $10^5$ CFU, $10^4$ and $10^6$ CFU, $10^4$ and $10^7$ CFU, $10^4$ and $10^8$ CFU, $10^4$ and $10^9$ CFU, $10^4$ and $10^{10}$ CFU, $10^4$ and $10^{11}$ CFU, $10^4$ and $10^{12}$ CFU, $10^5$ and $10^6$ CFU, $10^5$ and $10^7$ CFU, $10^5$ and $10^8$ CFU, $10^5$ and $10^9$ CFU, $10^5$ and $10^{10}$ CFU, $10^5$ and $10^{11}$ CFU, $10^5$ and $10^{12}$ CFU, $10^6$ and $10^7$ CFU, $10^6$ and $10^8$ CFU, $10^6$ and $10^9$ CFU, $10^6$ and $10^{10}$ CFU, $10^6$ and $10^{11}$ CFU, $10^6$ and $10^{12}$ CFU, $10^7$ and $10^8$ CFU, $10^7$ and $10^9$ CFU, $10^7$ and $10^{10}$ CFU, $10^7$ and $10^{11}$ CFU, $10^7$ and $10^{12}$ CFU, $10^8$ and $10^9$ CFU, $10^8$ and $10^{10}$ CFU, $10^8$ and $10^{11}$ CFU, $10^8$ and $10^{12}$ CFU, $10^9$ and $10^{10}$ CFU, $10^9$ and $10^{11}$ CFU, $10^9$ and $10^{12}$ CFU, $10^{10}$ and $10^{11}$ CFU, $10^{10}$ and $10^{12}$ CFU, or $10^{11}$ and $10^{12}$ CFU.

It is widely known that the causes of neoplastic disease are multifaceted and diverse, often leading to prevention and treatment strategies comprising multiple therapies to achieve optimum results. As such, the present invention may involve combining the live attenuated bacteria of the first and/or second composition with other known cancer therapies. Preferably, the live attenuated bacterium of the first and/or second composition may be administered in combination with an immunotherapy, radiotherapy, chemotherapy or an anti-cancer agent. The term "anti-cancer agent" as used herein refers to any agent that is effective in killing cancer cells, halting the division of cancer cells, or helps to prevent the recurrence of cancer cells, but is not considered to be an immunotherapy, radiotherapy or chemotherapy.

In a preferred embodiment, the live attenuated bacteria of the first and/or second composition may be administered in combination with an immunotherapy. Preferably, the immunotherapy may comprise a checkpoint inhibitor, an antigen specific T cell, an adoptive T cell therapy, a therapeutic antibody, a cancer vaccine or any other engineered cellular immunotherapy.

A "checkpoint inhibitor" is an agent, which acts on surface proteins, which are members of either the TNF receptor or B7 superfamilies, or others, including agents which bind to negative co-stimulatory molecules. Examples of such checkpoint inhibitors include, but are not limited to, CTLA-4, PD-1, TIM-3, BTLA, TIGIT, VISTA, LAG-3, and/or their respective ligands, including PD-L1.

Where the immunotherapy comprises a checkpoint inhibitor, the checkpoint inhibitor may be directed against CTLA-4, PD-1, PD-L1, LAG3, TIM3, BTLA, VISTA or TIGIT. In a preferred embodiment, the checkpoint inhibitor may be directed against CTLA-4, PD-1 or PD-L1. In some instances, the blocking agent may be ipilimumab (Yervoy®-targeting CTLA-4), nivolumab (Opdivo®-targeting PD-1), pembrolizumab (Keytruda®—targeting PD-1), atezolizumab (Tecentriq®-targeting PD-L1), cemiplimab (Libtayo®-targeting PD-1) or durvalumab (Imfinzi®-targeting PD-L1).

The terms "Programmed Death 1," "Programmed Cell Death 1," "Protein PD-1," "PD-1", CD279 and "PD1," are used interchangeably, and include variants, isoforms, species homologs of human PD-1, and analogs having at least one common epitope with PD-1. The complete PD-1 sequence can be found under GenBank Accession No. NP 005009.2.

The terms "PD-L1", "PDL1", "programmed death ligand 1", CD274 and "programmed cell death 1" are used interchangeably and taken to include variants, isoforms and species homologs of human PD-L1, and analogs having at least one common epitope with PD-L1. The complete PD-L1 sequence can be found under GenBank Accession No. NP 054862.1.

The terms "cytotoxic T lymphocyte-associated antigen-4," "CTLA-4," "CTLA4," CD152 and "CTLA-4 antigen" are used interchangeably, and include variants, isoforms, species homologs of human CTLA-4, and analogs having at least one common epitope with CTLA-4. The complete CTLA-4 sequence can be found under GenBank Accession No. NP_005205.2.

The terms "LAG-3", "LAG3", CD223 and "lymphocyte-activation gene 3" are used interchangeably and taken to include variants, isoforms and species homologs of human LAG-3, and analogs having at least one common epitope with LAG-3. The complete LAG-3 sequence can be found under GenBank Accession No. NP_002277.4.

The terms "TIM-3", "TIM3", "HAVCR2", "hepatitis A virus cellular receptor 2", CD366 and "T-cell immunoglobulin domain and mucin domain 3" are used interchangeably and taken to include variants, isoforms and species homologs of human TIM-3, and analogs having at least one common epitope with TIM-3. The complete TIM-3 sequence can be found under GenBank Accession No. NP_116171.3.

The terms "BTLA", "B and T lymphocyte attenuator" and "CD272" are used interchangeably and taken to include variants, isoforms and species homologs of human BTLA, and analogs having at least one common epitope with BTLA. The complete BTLA sequence can be found under GenBank Accession No. NP_861445.4.

The terms "VISTA", "V-set immunoregulatory receptor", "B7H5", "B7-H5", "PD-1H" and "V-domain Ig suppressor of T cell activation" are used interchangeably and taken to include variants, isoforms and species homologs of human VISTA, and analogs having at least one common epitope with VISTA. The complete VISTA sequence can be found under GenBank Accession No. NP_071436.1.

The terms "TIGIT", "T cell immunoreceptor with Ig and ITIM domains", "WUCAM" and "Vstm3" are used interchangeably and taken to include variants, isoforms and species homologs of human TIGIT and analogs having at least one common epitope with TIGIT. The complete TIGIT sequence can be found under GenBank Accession No. NP_776160.2.

The PD-L1/PD-1 signalling pathway is a primary mechanism of cancer immune evasion for several reasons. First, and most importantly, this pathway is involved in negative regulation of immune responses of activated T effector cells, found in the periphery. Second, PD-L1 is up-regulated in cancer microenvironments, while PD-1 is also up-regulated on activated tumour infiltrating T cells, thus possibly potentiating a vicious cycle of inhibition. Third, this pathway is intricately involved in both innate and adaptive immune regulation through bi-directional signalling. These factors make the PD-1/PD-L1 complex a central point through which cancer can manipulate immune responses and promote its own progression. As a result, the tumour is able to activate inhibitory immune checkpoint molecule pathways, resulting in a suppressed immune system and the continued unimpeded growth of cancerous cells. Following T-cell activation, CTLA-4 is transported to the surface where it competes with CD28 for the same ligands as on the antigen-presenting cells (APCs), resulting in suppression of CD28 and subsequent suppression of T-cell activation and proliferation. Targeting PD-1, PD-L1 and CTLA-4 aims to prevent these events from occurring.

Where the immunotherapy comprises an antigen-specific T cell, the antigen-specific T cell may be a result of adoptive T cell therapy. The term "adoptive cell therapy" is intended to refer to any therapy that involves the transfer/administration of cells into a subject, preferably a human. The cells may be autologous or allogeneic. Preferably, the cells are commonly derived from the immune system with the goal of improving immune functionality. Adoptive cell therapy may include, but is not limited to, CAR-T cell therapy (chimeric antigen receptor T-cell), TIL therapy (tumour infiltrating lymphocytes) and iPSC-derived therapy (induced pluripotent stem cells). It is particularly envisaged that the adoptive T cell therapy may be CAR-T cell therapy. In some instances, the CAR-T cell therapy will be directed against the antigen CD19, which is present in B-cell derived cancers. Accordingly, such therapy may be particularly suited for B-cell derived cancers, such as acute lymphoblastic leukemia (ALL) and diffuse large B-cell lymphoma (DLBCL). In other instances, the CAR-T cell therapy will be directed against tumour-associated antigens (TAAs) and are accordingly more suited for the treatment of solid tumours. Examples of such antigens include, but are not limited to, CD133, CD138, CEA, EGFR, EpCAM, GD2, GPC3, HER2, HerinCAR-PD1, MSLN, MG7, MUC1, LMP1, PSMA and PSCA. Such techniques will be known to those skilled in the art and the reader is directed to the review entitled "Adoptive cellular therapies: the current landscape" for further information (Rohaan et aL. 2019, Virchows Arch. 474(4): 449-461).

Where the immunotherapy comprises a therapeutic antibody, said therapeutic antibody may be directed at the cancer or tumour. The term "therapeutic antibody" as referred to herein includes whole antibodies and any antigen-binding fragment (i.e., "antigen-binding portion") or single chains thereof which results in a therapeutic effect. Such therapeutic antibodies may be directed at the checkpoint inhibitor molecules directed above or include agonistic antibodies directed at co-stimulatory molecule targets such as ICOS (inducible T cell costimulatory/CD278), GITR (glucocorticoid-induced TNF receptor/TNFRSF18/CD357/AITR), 4-1BB (CD137), CD27 and CD40. In some instances, it may be desirable for the subject to receive both types of therapeutic antibody.

The therapeutic antibody may be a monoclonal antibody, and even more preferred, a humanised or human monoclonal antibody. The term "monoclonal antibody" as used herein refer to a preparation of antibody molecules of single molecular composition. A monoclonal antibody composition displays a single binding specificity and affinity for a particular epitope. The term "human antibody", as used herein, is intended to include antibodies having variable regions in which both the framework and CDR regions are derived from human germline immunoglobulin sequences. The term "humanized antibody" is intended to refer to antibodies in which CDR sequences derived from the germline of another mammalian species, such as a mouse, have been grafted onto human framework sequences. Additional framework region modifications may be made within the human framework sequences.

Methods of obtaining such monoclonal antibodies are known to those skilled in the art. The therapeutic antibody may block an abnormal protein in a cancer cell, attach to specific proteins on cancer cells or be conjugated to a cytotoxic molecules, such as an anticancer drug. The latter flags the cancer cells to the immune system so that the abnormal cells can subsequently be targeted and destroyed by cellular components of the immune system. In some instances, the monoclonal antibody may also be a checkpoint inhibitor. For example, ipilimumab (Yervoy®), nivolumab (Opdivo®) and pembrolizumab (Keytruda®) are all monoclonal antibodies as well as checkpoint inhibitors. In other instances, the monoclonal antibody may be an agonistic antibody directed at a co-stimulatory molecule target, such as ICOS (inducible T-cell costimulatory/CD278), GITR (glucocorticoid-induced TNF receptor/TNFRSF18/CD357/AITR), 4-1 BB (CD137), CD27 and CD40. Examples of non-checkpoint inhibitor monoclonal antibodies for the treatment of cancer include, but are not limited to, trastuzumab (Herceptin®), bevacizumab (Avastin®), cetuximab (Erbitux®), panitumumab (Vectibix®), rituximab (Rituxan® and Mabthera®), alemtuzumab (Campath®), ofatumumab (Arzerra®), gemtuzumab ozogamicin (Mylotarg®) and brentuximab vedotin (Adcetris®).

The immunotherapy may comprise a cancer vaccine. The cancer vaccine may be a preventative vaccine or a treatment vaccine, preferably the vaccine is a treatment vaccine. The use of cancer vaccines teaches the immune system to recognise and destroy the antigens presented by the cancerous cells. Such vaccines may also comprise adjuvants to help boost the response even further.

The immunotherapy may comprise any other engineered cellular immunotherapy. In the context of the present invention, "any other engineered cellular immunotherapy" refers to any cell type that has been engineered in a manner that is designed to modulate the immune system or immune response in a subject to provide favourable outcomes in relation to cancer prevention or treatment. Examples of such cells include, but are not limited to, natural killer cells, macrophages, lymphocytes, stem cells and dendritic cells.

In a second aspect, the present invention provides for a method of treating, preventing, inhibiting, preventing recurrence, or controlling a neoplastic disease in a subject, wherein the method comprises simultaneously, separately or sequentially administering to the subject, (i) a first composition comprising a live attenuated bacterium and (ii) a second composition comprising a live attenuated bacterium, said bacterium being the same or different to that of the first composition, wherein the first composition is formulated for oral, intravenous, intranasal, intradermal or subcutaneous delivery to stimulate a systemic immune response in the subject and is for administration simultaneously, separately or sequentially with the second composition, and wherein the second composition is for administration locally to the site of the neoplastic disease.

The present invention therefore provides for a method of treating, preventing, inhibiting, preventing recurrence, or controlling a neoplastic disease in a subject, wherein said method comprises the live attenuated bacterium for use herein described.

Therefore, the method of the present invention may be used to reduce or inhibit metastasis of a primary tumour or cancer to other sites, or the formation or establishment of metastatic tumours or cancers at other sites distal from the primary tumour or cancer thereby inhibiting or reducing tumour or cancer relapse or tumour or cancer progression. Accordingly, the present invention provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumour or cancer, or metastasis, i.e., a therapeutic benefit or a beneficial effect.

The method of the present invention is therefore a combination therapy comprising administration of two compositions, the features of which are described above. Such a combination has the potential to elicit potent and durable immune responses in a subject, resulting in enhanced therapeutic benefit.

A therapeutic benefit or beneficial effect is any objective or subjective, transient, temporary, or long-term improvement in the condition or pathology, or a reduction in onset, severity, duration or frequency of an adverse symptom associated with or caused by cell proliferation or a cellular hyperproliferative disorder such as a neoplasia, tumour or cancer, or metastasis. It may lead to improved survival. A satisfactory clinical endpoint of a treatment method in accordance with the invention is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumour or cancer, or metastasis. A therapeutic benefit or improvement therefore may be, but is not limited to destruction of target proliferating cells (e.g., neoplasia, tumour or cancer, or metastasis) or ablation of one or more, most or all pathologies, adverse symptoms or complications associated with or caused by cell proliferation or the cellular hyperproliferative disorder such as a neoplasia, tumour or cancer, or metastasis. However, a therapeutic benefit or improvement need not be a cure or complete destruction of all target proliferating cells (e.g., neoplasia, tumour or cancer, or metastasis) or ablation of all pathologies, adverse symptoms or complications associated with or caused by cell proliferation or the cellular hyperproliferative disorder such as a neoplasia, tumour or cancer, or metastasis. For example, partial destruction of a tumour or cancer cell mass, or a stabilization of the tumour or cancer mass, size or cell numbers by inhibiting progression or worsening of the tumour or cancer, can reduce mortality and prolong lifespan even if only for a few days, weeks or months, even though a portion or the bulk of the tumour or cancer mass, size or cells remain.

Specific non-limiting examples of therapeutic benefit include a reduction in neoplasia, tumour or cancer, or metastasis volume (size or cell mass) or numbers of cells, inhibiting or preventing an increase in neoplasia, tumour or cancer volume (e.g., stabilizing), slowing or inhibiting neoplasia, tumour or cancer progression, worsening or metastasis, or inhibiting neoplasia, tumour or cancer proliferation, growth or metastasis.

An invention method may not take effect immediately. For example, treatment may be followed by an increase in the neoplasia, tumour or cancer cell numbers or mass, but over time eventual stabilization or reduction in tumour cell mass, size or numbers of cells in a given subject may subsequently occur.

Additional adverse symptoms and complications associated with neoplasia, tumour, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of an adverse symptom or complication associated with or caused by a cellular hyperproliferative disorder, an improvement in the subjects quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In an additional embodiment, a method prolongs or extends lifespan (survival) of the subject. In a further embodiment, a method improves the quality of life of the subject.

A therapeutic benefit may also include the prevention of recurrence of neoplasia, tumour, cancer and metastasis, for example, wherein said neoplasia, tumour, cancer and metastasis has been surgically or chemically ablated.

The present invention may be suited to individuals who have been refractory to previous prevention and/or treatment strategies. By "refractory", we intend a reference to any neoplastic disease that does not respond to treatment. It is also envisaged that the present invention may be suited to individuals who have previously been low responders, moderate responders or high responders to previous treatment.

The first and second composition will typically be administered to the subject in a composition that comprises an effective amount of the live attenuated bacteria, for example, the *Salmonella* serovar *typhi* ZH9 strain, and further comprises a pharmaceutically acceptable carrier/adjuvant/diluent or excipient. The phrases "pharmaceutically" and "pharmacologically acceptable" refer to molecular entities and compositions that do not produce an adverse, allergic or other untoward reaction when administered to an animal, such as, for example, a human, as appropriate. Such preparations will be known to those skilled in the art. Moreover, for animal (e.g., human) administration, it will be understood that preparations should meet sterility, pyrogenicity, general safety and purity standards, as applicable.

As used herein, "pharmaceutically acceptable carrier/adjuvant/diluent/excipient" includes any and all solvents, dispersion media, coatings, surfactants, antioxidants, preservatives {e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Examples include, but are not limited to disodium hydrogen phosphate, soya peptone, potassium dihydrogen phosphate, ammonium chloride, sodium chloride, magnesium sulphate, calcium chloride, sucrose, borate buffer, sterile saline solution (0.9% NaCl) and sterile water.

The first and/or second composition may also comprise additional components intended for enhancing an immune response. Examples of such additional components include but are not limited to; aluminium salts such as aluminium hydroxide, aluminium oxide and aluminium phosphate, oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (e.g., mureins, mucopeptides, or glycoproteins such as N-*Opaca*, muramyl dipeptide [MDP], or MDP analogs), proteoglycans (e.g., extracted from *Klebsiella pneumoniae*), streptococcal preparations (e.g., OK432), muramyldipeptides, Immune Stimulating Complexes (the "Iscoms" as disclosed in EP 109 942, EP 180 564 and EP 231 039), saponins, DEAE-dextran, neutral oils (such as miglyol), vegetable oils (such as *arachis* oil), liposomes, polyols, the Ribi adjuvant system (see, for instance, GB-A-2 189 141), vitamin E, Carbopol, interferons (e.g., IFN-alpha, IFN-gamma, or IFN-beta), interleukins, particularly those that stimulate cell mediated immunity (e.g., IL-2, IL-3, IL-4, IL-5, IL-6, IL-7, IL-8, IL-9, IL-10, IL-11, IL-12, IL-13, IL-14, IL-15, IL-16, IL-17, IL-18, IL-21) or chemokines (e.g. CXCL9, CXCL10, CXCL11, CCL5, CCL2, CX3CL1).

The invention is further described with reference to the following non-limiting examples:

EXAMPLES

Example 1

ZH9 interaction with urothelial cancer cells was investigated using in vitro invasion assays and flow cytometry staining for intracellular *Salmonella* common antigen (CSA-1) and propidium iodide for cell death. Therapeutic efficacy of ZH9 against bladder tumour growth was established in the murine orthotopic, syngeneic MB49 bladder tumour model. Tumour-bearing animals were treated with a single intravesical dose of ZH9 or OncoTice BCG and long-term survival comparisons were evaluated by log-rank (Mantel-Cox) test. Local immune responses were analysed by flow cytometry staining of disaggregated mouse bladders following treatment of healthy mice.

Mice treated with a single dose of ZH9 2 days after MB49 tumour inoculation demonstrated significant survival benefit compared to both vehicle treated (median survival 49.5 vs. 31 days, p=0.003) and BCG treated animals (median survival 49.5 vs. 27.5 days, p<0.001). Even in a more stringent model with treatment 4 days after tumour inoculation, ZH9 showed significant efficacy (median survival 30 vs. 20.5 (p=0.003) and 23.5 (p=0.025) days for vehicle and BCG, respectively). Surviving ZH9 treated animals, unlike naïve controls, were resistant to further bladder inoculation with MB49 tumour cells, suggesting a lasting anti-tumour immunity results from ZH9 treatment (100% vs. 31.5% median survival day 45, p=0.01). In vitro, intracellular flow cytometry in human (UMUC3, T24, RT4, 5637) and mouse (MB49) urothelial cancer cell lines showed that ZH9 invaded and induced cell death in all cell types 24 hrs after a 1 hr exposure. In vivo, a single intravesical treatment with ZH9 resulted in a strong cellular immune response characterised at day 7 by strong recruitment of monocytes, NK cells, CD4+ and CD8+ T cells and dendritic cells with an activated, cross-presenting (Ly6C+, CD103+) phenotype, in all cases of greater magnitude and duration than after a single treatment with an equivalent dose of BCG.

Accordingly, live-attenuated *Salmonella* strain ZH9 has been shown to demonstrate a clear survival benefit over the standard-of-care in an orthotopic bladder cancer model, likely via both direct tumour cell killing and induction of robust cellular immune responses, and as such indicate significant therapeutic potential of ZH9 in bladder cancer.

Example 2

Figure 1A:
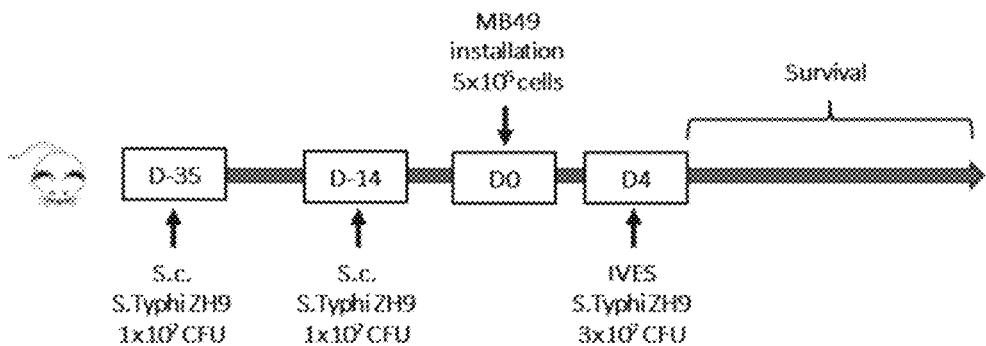
FIG. 1A shows a schematic demonstrating the timeline of subcutaneous systemic and local administration of *Salmonella typhi* in an orthotopic murine MB49 bladder cancer model. S.c, subcutaneous. IVES, intravesical.

Prior Systemic Priming with Subcutaneous *Salmonella typhi* Enhances the Efficacy of Local Bladder *Salmonella typhi* Treatment The purpose of the study herein described was to evaluate the effect of a subcutaneous (s.c.) priming with the attenuated *Salmonella typhi* strain ZH9 before intravesical (ives) ZH9 treatment on levels of mice surviving in a non-muscle invasive bladder cancer model (See FIG. 1A).

As detailed below, the inventors of the application have surprisingly shown that mice treated with both systemic and local administration of *Salmonella typhi* show improved survival rates.

Materials and Methods

Mouse Cells

The MB49 cell-line (provided by Prof. A. Loskog, Uppsala University, Sweden) is derived from a carcinogen induced urothelial carcinoma in male C57Bl/6 mice (Summerhayes, Journal of the National Cancer Institute, 62(4): 1017-1023, 1979). Luciferase-expressing (MB49-luc) were generated by transfection with lentiviral vectors encoding for firefly luciferase, (provided by Prof. D. Trono, EPFL, Lausanne, Switzerland).

The MB49 Orthotopic Bladder Tumour Model

Seven to ten-week-old female C57Bl/6 wild type mice (Charles River) were used and all experiments were performed in accordance with Swiss law and with approval of the Cantonal Veterinary Office of Canton de Vaud, Switzerland. Bladder tumours were established in deeply anesthetized mice that were urethrally catheterized using Introcan 24Gx3/4 catheters (Braun, Melsungen, Germany). A 15 minute pre-treatment with 100 µl 22% ethanol was performed before instillation of 500,000 MB49-luc cells in 50 µl. MB49-luc tumour growth was monitored by bioluminescence 15 minutes after intraperitoneal (I.P) injection of D-Iuciferin (Promega, L8220, 150 µg/g of body weight) in the Xenogen imaging system (Xenogen/IVIS Caliper Life Science, kindly provided by cellular imaging facility, CIF/UNIL, Lausanne, Switzerland). 100% of the mice developed bladder tumours. Bioluminescence monitoring of MB49-luc tumours is very efficient for assessing tumour establishment and growth during the first 3 weeks, however uncontrolled loss of luminescence of the growing tumours can then often appear (Jurczok et al., BJU International, 101(1):120-124, 2008), requiring additional monitoring by palpation, hematuria and overall health status of the mice. Mice were sacrificed when the approved termination were reached.

Bacteria Preparation

Dilutions of the attenuated *Salmonella typhi* strain (ZH9) were prepared in PBS as required to achieve $3\times10^7$ CFU/50 µl for ives instillation and $1\times10^7$CFU/100 µl for s.c. injection.

Intravesical Treatments

50 µl bacterial suspensions volumes were instilled by urethral catheterization, as described above. The retention time in the bladder was 1 hour, until the mice awaking from the anesthesia spontaneously urinated. In this stringent setting, a single intravesical treatment-instillation was administered at day 5 (4 days after intravesical tumour-cell instillation). Tumours were detectable by bioluminescence at day 5.

Survival rates were monitored over 100 days. The results are reflective of five separate studies, demonstrating the reproducibility of said results.

Results

Figure 1B:
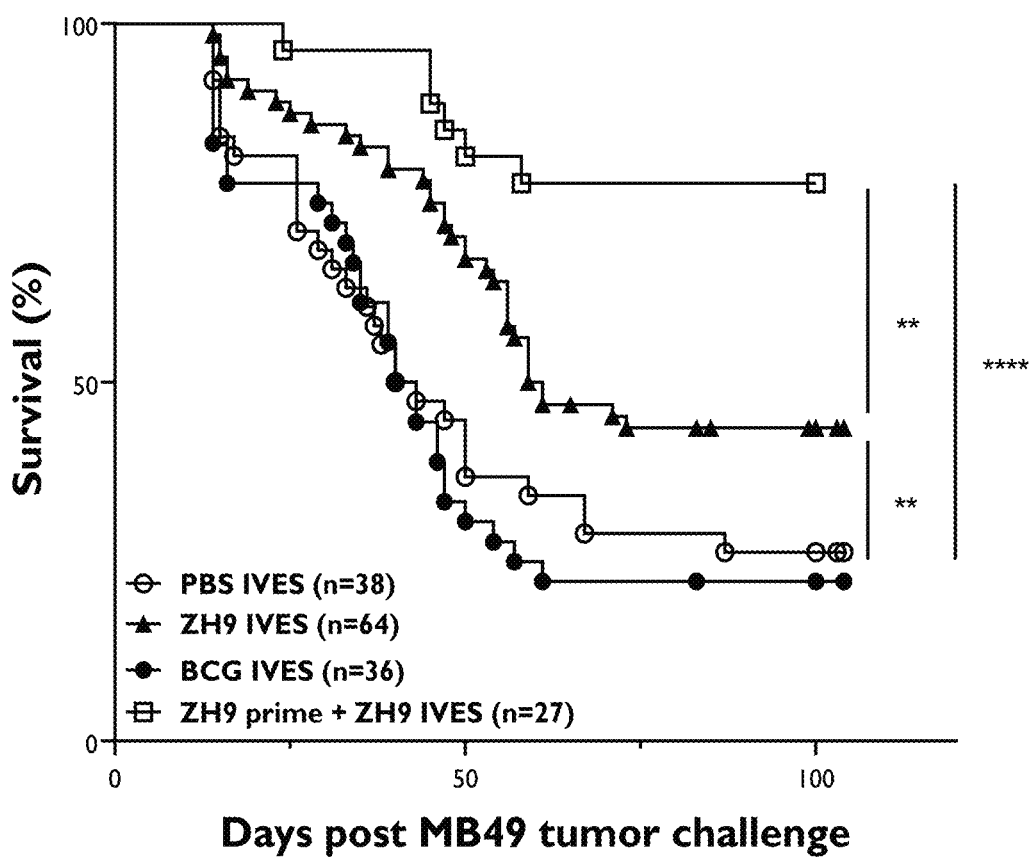

Mice that received local administration (ives) of ZH9 to the bladder had improved survival at study termination compared to mice that were treated with ives PBS (p<0.01). An even greater proportion of mice that had received s.c. ZH9 in addition to ives ZH9 survived (p<0.01) (See FIG. 1B). Statistics are log-rank (Mantel-Cox) test. The mice treated with both systemic and local bladder administration of Salmonella showed terminal survival rates of 77% vs 43% for local bladder ZH9 administration alone and vs 26% for local bladder PBS treatment.

Example 3

Systemic Priming with Subcutaneous Salmonella typhi Enhances Desirable Bladder Cellular Immune Response to Local Salmonella typhi Treatment The purpose of the study herein described was to evaluate, by flow cytometry, levels of immune cell infiltration in the bladder of mice that had received subcutaneous systemic priming with a Salmonella typhi strain (ZH9) prior to local intravesical administration of a Salmonella typhi strain (ZH9) (See FIG. 2).

As detailed below, the inventors of the present invention have surprisingly shown that systemic priming increases peak magnitude and longevity of myeloid and lymphoid immune responses in the bladder and that undesirable neutrophilic inflammation is not enhanced.

Materials and Methods

Female C57BL/6 mice were treated subcutaneously with $1 \times 10^7$ CFU Salmonella typhi ZH9 or PBS control on days −35 and −14. On day 1, mice were treated with $3 \times 10^7$ CFU Salmonella typhi ZH9 or PBS control intravesically. At the indicated timepoints (24 hrs and 7 days) after treatment, bladder tissue was harvested and digested with collagenase/dispase/DNase (See FIG. 2). A single cell suspension was generated and cells were stained for flow cytometry analysis.

Bacteria Preparation

Dilutions of the attenuated Salmonella typhi strain (ZH9) were made in PBS as required to achieve $3 \times 10^7$ CFU/50 µl for ives instillation and $1 \times 10^7$ CFU/100 µl for s.c. injection.

Intravesical Treatments

Seven to ten-week-old female C57Bl/6 wild type mice (Charles River) were used and all experiments were performed in accordance with Swiss law and with approval of the Cantonal Veterinary Office of Canton de Vaud, Switzerland. Intravesical instillation were performed in deeply anesthetized mice that were urethrally catheterized using Introcan 24Gx3/4 catheters (Braun, Melsungen, Germany). 50 µl bacterial suspensions volumes were instilled. The retention time in the bladder was ca 1 hour, until the mice awaking from the anesthesia spontaneously urinated.

Bladder Preparation

Mice were sacrificed by $CO_2$ inhalation to collect the bladder. Single-cell suspensions were obtained by mincing in DL-dithiothreitol (Sigma Merck KGaA) and digesting with 1 mg/mL collagenase/dispase (Roche, Basel, Switzerland) and 0.1 mg/ml DNAse I (Sigma Merck KGaA) with 20% Fetal Calf Serum (Gibco, MA, USA). The recovered cells were used for immunostaining.

Immunostaining and Flow Cytometry Analysis

The monoclonal anti-mouse antibodies used were: Anti-CD3-PE (17A2), Anti-CD3-PerCP/Cy5.5 (17A2), Anti-Ly6G-PE/Cy7 (1A8), Anti-Ly6C-AF700 (HK1.4), Anti-CD8-APC/Cy7 (53-6.7) Anti-CD103-PcBlue (2E7) Anti-CD11 b-FITC (M1/70), Anti-XCR1-APC (ZET) (Biolegend); Anti-CD4-APC (RM4-5), Anti-CD8-PE (53-6.7) (BD Biosciences), Anti-CD11c-PE-eF610 (N418), Anti-CD45-FITC (30-F11), Anti-CD45-PerCP/Cy5.5 (30-F11), Anti-CD11 b-AF700 (M1/70), Anti-CD335-eF450 (29A1.4) (eBioscience, Thermo Fisher Scientific, MA, USA). The following Isotype controls were used: rat IgG2a, κ isotype control-APC-Cy7 (RTK2758), rat IgG2a, κ isotype control-APC (RTK2758) (Biolegend), Arm hamster IgG isotype control-PE-eF610 (eBio99Arm) (eBioscience).

Dead cells were excluded by a live/dead fixable aqua dead cell stain kit (Invitrogen Thermo Fisher Scientific, MA, USA). Cell acquisition and analysis were performed using Gallios Flow Cytometer (Beckman Coulter, Nyon, Switzerland) and FlowJo software (Tree Star, Ashland, OR), respectively.

Results

Immune filtration is significantly increased by priming with s.c. ZH9 when administered before ives ZH9 (See FIGS. 3A, 3B and 3C). This is particularly evident 7 days after instillation. Priming with ZH9 particularly increased T cells and NK cells 7 days after ives instillation, while myeloid cells were less altered. Both CD4+ and CD8+ T cells are significantly increased by priming with ZH9, 7 days after ives ZH9 instillation (See FIGS. 3A and 3B). Neutrophils were not altered by priming with ZH9, whilst monocytes were significantly increased, particularly 24 h after ives ZH9 (See FIGS. 3A and 3B).

Example 4

Systemic Priming with Oral Salmonella Typhimurium Enhances Desirable Cellular Immune Response to Local Salmonella typhi Treatment The purpose of the study herein described was to determine changes in T cell numbers, phenotype and function in tumour-bearing mice (in a murine colon cancer model) following oral systemic priming with a Salmonella Typhimurium strain (MD58) in combination with a local intra-tumoural treatment with a Salmonella typhi strain (ZH9).

Materials and Methods

Bacterial Cell Preparation

Dilutions of the attenuated Salmonella Typhimurium strain (MD58) were made in PBS as required to achieve $1 \times 10^9$ CFU/100 µl for oral gavage. Dilutions of the attenuated Salmonella typhi strain (ZH9) were made in PBS as required to achieve $1 \times 10^7$ CFU/40 µl for intra-tumoral injections.

MC38 Colon Cancer Model

Seven to fourteen-week old female C57BL/6 mice were used for all experiments. The MC38 colon cancer cell line was purchased from Kerafast, Inc. and maintained within the exponential growth phase leading up to injection. Cells were prepared by trypsinization, washed in plain media, and viable cells counted via an automated cell counter. Prior to tumour cell implantation each mouse was anaesthetised using 1-2% isoflurane, and injection area shaved and cleaned. $6 \times 10^5$ MC38 cells in 200 µL serum-free media were subcutaneously injected in the rear flank using a 27G syringe. Tumour burden was monitored at regular intervals such that it did not exceed permitted level by Prokarium's Home Office licence. Mice were treated with oral Salmonella Typhimurium (7 days prior to MC38 inoculation), followed by intra-tumoural treatment with Salmonella typhi (14 days after MC38 inoculation, or with intra-tumoural treatment with *Salmonella typhi* (14 days after MC38 inoculation) alone (See FIG. 4). The effect of the oral systemic prime of *Salmonella* Typhimurium on T cell infiltration, phenotype and functional status was assessed on 1 day and 7 days following intra-tumoural treatment with *Salmonella Typhi*.

Tissue Isolation and Flow Cytometry

Tumours and spleens were excised and mechanically disassociated using a strainer and syringe plunger. The lysates were then filtered through a 70 µm cell strainer, and red blood cells lysed. Tumours were additionally processed using a 35% Percoll solution to remove cellular debris. Cell pellets were resuspended in appropriate buffers for downstream analysis. For flow cytometric analysis, dead cells were excluded by a live/dead fixable aqua dead cell stain kit (Thermo Fisher), and then stained with the following monoclonal antibodies: anti-CD90.2 (53-2.1; Biolegend), Anti-CD4 (RM4-5; Thermo Fisher), Anti-CD8α (53-6.7; Biolegend), Foxp3 (FJK-16s; Thermo Fisher), IFNγ (XMG1.2; Biolegend), and Ki-67 (16A8; Biolegend). Cell acquisition and analysis were performed using an ATTUNE NXT cytometer (Thermo Fisher) and FlowJo software (Tree Star), respectively.

Assessment of Number of Tumour-Infiltrating CD8$^+$ And CD4$^+$ T Cells

Seven to nine-week old female C57BL/6 mice were either immunized with $1 \times 10^9$ CFU of *Salmonella* Typhimurium MD58 per os (PO, "by mouth") or left untreated. 7 days later, $6 \times 10^5$ MC38 (colon) tumour cells were subcutaneously inoculated in all mice. 14 days later all mice received an intra-tumoral (IT) dose of $1 \times 10^7$ CFU of *Salmonella typhi* ZH9. Tumours and spleens were harvested 1 day and 7 days post IT treatment, with n=3 or 4 mice per group per timepoint. Tumours were mechanically disassociated, filtered, and single cell suspension analyzed by flow cytometry on an Attune NXT cytometer. Cells were stained for surface markers followed by fixation/permeabilization, and then stained for intracellular molecules. Indicated T cell populations were gated on FSC/SSC, singlets, viability dye-, CD90$^+$ followed by either CD4, CD8, or CD4 and Foxp3. Absolute cell counts were normalized to weights of each tumour.

Assessment of T Cell Proliferation in the Tumour and in Periphery

Seven to nine-week old female C57BL/6 mice were either immunized with $1 \times 10^9$ CFU of *Salmonella* Typhimurium MD58 per os (PO, "by mouth") or left untreated. 7 days later, $6 \times 10^5$ MC38 (colon) tumour cells were subcutaneously inoculated in all mice. 14 days later all mice received an intra-tumoral (IT) dose of $1 \times 10^7$ CFU of *Salmonella typhi* ZH9. Tumours and spleens were harvested 1 day and 7 days post IT treatment, with n=4 mice per group per timepoint. Tumours were mechanically disassociated, filtered, and single cell suspension analyzed by flow cytometry on an Attune NXT cytometer. Cells were stained for surface markers followed by fixation/permeabilization, and then stained for intracellular molecules. CD8 T cells were gated on FSC/SSC, singlets, viability dye-, CD90+, and CD8+. CD4 T cells were gated on FSC/SSC, singlets, viability dye-, CD90+, CD4+, and Foxp3-. Proliferating T cells were defined as Ki-67+ and are represented as a percentage of total CD8 T cells.

Assessment of Functional Potential of CD8$^+$ and CD4$^+$ T Cells

Seven to nine-week old female C57BL/6 mice were either immunized with $1 \times 10^9$ CFU of *Salmonella* Typhimurium MD58 per os (PO, "by mouth") or left untreated. 7 days later, $6 \times 10^5$ MC38 (colon) tumour cells were subcutaneously inoculated in all mice. 14 days later all mice received an intra-tumoral (IT) dose of $1 \times 10^7$ CFU of *Salmonella typhi* ZH9. Tumours and spleens were harvested 1 day and 7 days post IT treatment, with n=4 mice per group per timepoint. Tumours were mechanically disassociated, filtered, and single cell suspension analyzed by flow cytometry on an Attune NXT cytometer. Cells were stained for surface markers followed by fixation/permeabilization, and then stained for intracellular molecules. CD8 T cells were gated on FSC/SSC, singlets, viability dye-, CD90+, and CD8+. CD4 T cells were gated on FSC/SSC, singlets, viability dye-, CD90+, CD4+, and Foxp3-. Proliferating T cells were defined as Ki-67+ and are represented as a percentage of total CD8 T cells. For assessment of cytokine production capacity, cells were stimulated for 4 hours at 37° C. in the presence of Cell Activation Cocktail with Brefeldin A (Biolegend; 423303). After stimulation, cells were stained for surface markers followed by fixation/permeabilization, and then stained for intracellular molecules. CD8 T cells were gated on FSC/SSC, singlets, viability dye-, CD90+, and CD8+. IFNγ+CD8 T cells are represented as a percentage of total CD8 T cells. CD4 T cells were gated on FSC/SSC, singlets, viability dye-, CD90+, CD4+, and Foxp3-. IFNγ+ CD4 T cells are represented as a percentage of total CD4 T cells. The functional potential is measured as % of T cells able to produce IFNγ following stimulation with T cell activation cocktail (PMA+ionomycin+Brefeldin A).

Results

Numbers of tumour-infiltrating CD8 and CD4 T cells, but not regulatory T cells (Treg), were found to be increased after systemic priming with oral *Salmonella Typhimurium* in combination with intra-tumoral *Salmonella typhi* treatment as compared to intra-tumoral treatment alone (See FIGS. 5A and 5B). Additionally, T cell proliferation in the tumour and in the periphery is shown to be increased following systemic priming with oral *Salmonella* Typhimurium in combination with intra-tumoral *Salmonella typhi* treatment as compared to intra-tumoral treatment alone, suggesting activation of the adaptive immune system, both locally and systemically (See FIGS. 6 and 7). The functional potential of CD8 and CD4 cells was also shown to be increased in mice treated with systemic priming with oral *Salmonella* Typhimurium in combination with intra-tumoral *Salmonella typhi* treatment as compared to intra-tumoral treatment alone (See FIGS. 8 and 9).

The examples herein disclosed demonstrate that systemic administration of *Salmonella* followed by local administration of *Salmonella* enhances the efficacy of local administration of *Salmonella*. The inventors have also demonstrated that the combination of systemic administration and local administration of *Salmonella* induce a stronger immune response than that seen with local administration of *Salmonella* alone, likely driving anti-tumour activity. Furthermore, the inventors have herein demonstrated that the effects exemplified herein are seen across multiple *Salmonella* strains, multiple modes of systemic and local administration, and in multiple cancer models.

The invention claimed is:

1. A method of treating, reducing, inhibiting, or controlling a neoplastic disease in a subject, wherein the method comprises administering to the subject (i) a first composition comprising a live attenuated strain of *Salmonella enterica*, and (ii) a second composition comprising a live attenuated strain of *Salmonella enterica*, said strain of *Salmonella enterica* being the same or different to that of the first composition, wherein the first composition is administered orally, intravenously, intranasally, intradermally or via subcutaneous delivery to stimulate a systemic immune response in the subject, and wherein the first composition is administered simultaneously, separately or sequentially with the second composition, and wherein the second composition is for administration locally to the site of the neoplastic disease.

2. The method according to claim 1, wherein the live attenuated strain of *Salmonella enterica* is *Salmonella enterica* serovar *typhi* and/or *Salmonella enterica* serovar Typhimurium.

3. The method according to claim 1, wherein the live attenuated strain of *Salmonella enterica* of the first composition and/or the live attenuated strain of *Salmonella enterica* of the second composition comprises a genetically modified non-natural strain of *Salmonella enterica*.

4. The method according to claim 3, wherein the genetically modified non-natural strain of *Salmonella enterica* comprises an attenuating mutation in a *Salmonella* Pathogenicity Island 2 (SPI-2) gene and/or an attenuating mutation in a second gene.

5. The method according to claim 1, wherein the neoplastic disease is a solid cancer and/or a haematological malignancy.

6. The method according to claim 5, wherein the solid cancer and/or the haematological malignancy is a cancer selected from prostate cancer, oesophageal cancer, liver cancer, renal cancer, lung cancer, breast cancer, colorectal cancer, bladder cancer, breast cancer, pancreatic cancer, brain cancer, mesothelioma, hepatocellular cancer, lymphoma, leukaemia, gastric cancer, cervical cancer, ovarian cancer, thyroid cancer, melanoma, carcinoma, head and neck cancer, skin cancer or sarcoma, preferably wherein the neoplastic disease is associated with a cancer selected from bladder cancer, lung cancer, mesothelioma, hepatocellular cancer, melanoma, oesophageal cancer, gastric cancer, ovarian cancer, colorectal cancer, head and neck cancer or breast cancer, more preferably wherein the neoplastic disease is associated with a cancer selected from bladder cancer or colorectal cancer.

7. The method according to claim 5, wherein the neoplastic disease is bladder cancer, or wherein the neoplastic disease is non-muscle invasive bladder cancer or muscle invasive bladder cancer.

8. The method according to claim 1, wherein the second composition is administered via local instillation, intraperitoneally, intrapleurally, intravesically, peritumoral injection or intratumoural injection.

9. The method according to claim 1, wherein the first composition is a vaccine.

10. The method according to claim 1, wherein the live attenuated strain of *Salmonella enterica* of the first composition is administered to the subject prior to the live attenuated strain of *Salmonella enterica* of the second composition.

11. The method according to claim 1, wherein the live attenuated strain of *Salmonella enterica* of the first composition is *Salmonella enterica* serovar *typhi* and the live attenuated strain of *Salmonella enterica* of the second composition is *Salmonella enterica* serovar *typhi*.

12. The method according to claim 11, wherein the live attenuated strain of *Salmonella enterica* of the first composition is *Salmonella enterica* serovar *typhi* ZH9 and the live attenuated strain of *Salmonella enterica* of the second composition is *Salmonella enterica* serovar *typhi* ZH9.

13. The method according to claim 1, wherein the live attenuated strain of *Salmonella enterica* of the first composition is *Salmonella enterica* serovar Typhimurium and the live attenuated strain of *Salmonella enterica* of the second composition is *Salmonella enterica* serovar *Typhi*.

14. The method according to claim 13, wherein the live attenuated strain of *Salmonella enterica* of the first composition is *Salmonella enterica* serovar Typhimurium MD58 and the live attenuated strain of *Salmonella enterica* of the second composition is *Salmonella enterica* serovar *typhi* ZH9.

15. The method according to claim 1, wherein the live attenuated strain of *Salmonella enterica* of the first and/or second composition is administered in combination with an immunotherapy, radiotherapy, chemotherapy or an anticancer agent, preferably wherein the immunotherapy comprises a checkpoint inhibitor, an antigen specific T cell, an adoptive T cell therapy, a therapeutic antibody, a cancer vaccine or any other engineered cellular immunotherapy.

16. The method according to claim 3, wherein the genetically modified non-natural strain of *Salmonella enterica* comprises an attenuating mutation in a *Salmonella* Pathogenicity Island 2 (SPI-2) gene and an attenuating mutation in a second gene.

* * * * *